United States Patent
Bloom

(10) Patent No.: US 11,591,380 B2
(45) Date of Patent: Feb. 28, 2023

(54) GLUCAGON-LIKE PEPTIDES

(71) Applicant: IP2IPO INNOVATIONS LIMITED, London (GB)

(72) Inventor: Stephen Robert Bloom, London (GB)

(73) Assignee: IP2IPO INNOVATIONS LIMITED, London (GB)

( * ) Notice: Subject to any disclaimer, the term of this patent is extended or adjusted under 35 U.S.C. 154(b) by 0 days.

(21) Appl. No.: 16/769,774

(22) PCT Filed: Dec. 4, 2018

(86) PCT No.: PCT/GB2018/053512
§ 371 (c)(1),
(2) Date: Jun. 4, 2020

(87) PCT Pub. No.: WO2019/110981
PCT Pub. Date: Jun. 13, 2019

(65) Prior Publication Data
US 2021/0002344 A1    Jan. 7, 2021

(30) Foreign Application Priority Data

Dec. 4, 2017 (GB) .................................... 1720187

(51) Int. Cl.
| | | |
|---|---|---|
| C07K 14/605 | (2006.01) | |
| A61P 3/04 | (2006.01) | |
| A61K 9/00 | (2006.01) | |
| A61K 38/26 | (2006.01) | |

(52) U.S. Cl.
CPC .......... *C07K 14/605* (2013.01); *A61K 9/0019* (2013.01); *A61K 38/26* (2013.01); *A61P 3/04* (2018.01)

(58) Field of Classification Search
CPC .................................. C07K 14/605; A61P 3/04
See application file for complete search history.

(56) References Cited

U.S. PATENT DOCUMENTS

| | | |
|---|---|---|
| 4,179,337 A | 12/1979 | Davis et al. |
| 5,936,092 A | 8/1999 | Shen et al. |
| 6,093,692 A | 7/2000 | Shen et al. |
| 6,225,445 B1 | 5/2001 | Shen et al. |
| 6,410,707 B2 | 6/2002 | Wagner et al. |
| 9,764,003 B2 * | 9/2017 | Jensen ....................... A61P 3/04 |

FOREIGN PATENT DOCUMENTS

| | | |
|---|---|---|
| JP | 2016-526012 A | 9/2016 |
| WO | WO 2013/004983 A1 | 1/2013 |
| WO | WO 2014/041375 A1 | 3/2014 |
| WO | WO 2014/096145 A1 | 6/2014 |
| WO | WO 2014/170496 A1 | 10/2014 |
| WO | WO 2015/132599 A1 | 9/2015 |
| WO | WO 2016/198624 A1 | 12/2016 |
| WO | WO 2017/178829 A1 | 10/2017 |

OTHER PUBLICATIONS

Perfetti et al., Eur. J. Endocr. 143, 717-725, 2000.*
Gutniak et al., New England J. Med. 30 326:1316-1322, 1992.*
Centers for Disease Control and Prevention, "National Diabetes Statistics Report: Estimates of Diabetes and its Burden in the United States," 2014, pp. 1-12.
Centers for Disease Control and Prevention, "National Health and Nutrition Examination Survey: NHANES 2011-2012 Overview," Date Unknown, three pages, [Online] [Retrieved on Feb. 19, 2021] Retrieved from the Internet <URL https://wwwn.cdc.gov/nchs/nhanes/continuousnhanes/overview.aspx?BeginYear=2011>.
Centers for Disease Control and Prevention, "National Health and Nutrition Examination Survey: NHANES 2009-2010 Overview," Date Unknown, four pages, [Online] [Retrieved on Feb. 19, 2021] Retrieved from the Internet <URL https://wwwn.cdc.gov/nchs/nhanes/ContinuousNhanes/overview.aspx?BeginYear=2009>.
Jameson, B.A. et al., "The antigenic index: a novel algorithm for predicting antigenic determinants," Cabios, vol. 4, No. 1, 1988, pp. 181-186.
Jéquier, E., "Energy, obesity, and body weight standards," American Journal of Clinical Nutrition, vol. 45, May 1987, pp. 1035-1036.
Kenchaiah, S. et al., "Obesity and the Risk of Heart Failure," The New England Journal of Medicine, vol. 347, No. 5, Aug. 1, 2002, pp. 305-313.
Kolaskar, A.S. et al., "A semi-empirical method for prediction of antigen determinants on protein antigens," FEBS, vol. 276, Dec. 1990, pp. 172-174.
Kopelman, P.G., "Obesity as a medical problem," Nature, vol. 404, Apr. 6, 2000, pp. 635-643.
Langer, R., "New methods of drug delivery," Science, vol. 249, Iss. 4976, Sep. 28, 1990, pp. 1527-1533.
Lim, E.L. et al., "Reversal of type 2 diabetes: normalisation of beta cell function in association with decreased pancreas and liver triacylglycerol," Diabetologia, vol. 54, Jun. 9, 2011, pp. 2506-2514.
Lyznicki, J. M. et al., "Obesity: assessment and management in primary care," Am Fam Physician 63(11), Jun. 2001, pp. 2185-2196.
Rissanen, A. et al., "Risk of disability and mortality due to overweight in a Finnish population," British Medical Journal, vol. 301, Oct. 13, 1990, pp. 835-837.
Saudek, C.D. et al., "A preliminary trial of the programmable implantable medication system for insulin delivery," The New England Journal of Medicine 321 (9), Aug. 31, 1989, pp. 574-579.
Sefton, M.V., "Implantable pumps," Critical Reviews in Biomedical Engineering, vol. 14, Iss. 3, 1987, pp. 201-240.

(Continued)

*Primary Examiner* — Gyan Chandra
(74) *Attorney, Agent, or Firm* — Fenwick & West LLP

(57) ABSTRACT

The invention provides novel compounds which are peptide hormone analogues, and which are useful in treating disorders such as diabetes and obesity. The compounds of the general sequence recited in the specification possess a tailored profile with regards to potency properties at the glucagon and GLP-1 receptors. With regard to in vivo properties, administration of example peptides of the invention has been shown, in animal models, to result in increased weight loss.

20 Claims, 33 Drawing Sheets
Specification includes a Sequence Listing.

(56) References Cited

OTHER PUBLICATIONS

Teramoto, S. et al., "Exendin-4, a glucagon-like peptide-1 receptor agonist, provides neuroprotection in mice transient focal cerebral ischemia," Journal of Cerebral Blood Flow & Metabolism, vol. 31, Apr. 13, 2011, pp. 1696-1705.
United Kingdom Intellectual Property Office, Office Action, GB Patent Application No. 1720187.2, Aug. 24, 2018, five pages.
Wang, Y. et al., "Parenteral Formulations of Proteins and Peptides: Stability and Stabilizers," Journal of Parenteral Science and Technology, Technical Report No. 10, Supplement 1988, vol. 42, No. 2S, pp. S4-S25.
PCT International Search Report and Written Opinion, International Application No. PCT/GB2018/053512, dated Feb. 26, 2019, 11 Pages.

* cited by examiner

| Example No. SEQ ID NO | Amino Acid Residue Position | | | | | | | | | |
|---|---|---|---|---|---|---|---|---|---|---|
| | 1 | 2 | 3 | 4 | 5 | 6 | 7 | 8 | 9 | 10 |
| 1 | His | AIB | His | Gly | Thr | Phe | Thr | Ser | Asp | Tyr |
| 2 | His | AIB | His | Gly | Thr | Phe | Thr | Ser | Asp | Tyr |
| 3 | His | AIB | His | Gly | Thr | Phe | Thr | Ser | Asp | Tyr |
| 4 | His | AIB | His | Gly | Thr | Phe | Thr | Ser | Asp | Tyr |
| 5 | His | AIB | His | Gly | Thr | Phe | Thr | Ser | Asp | Tyr |
| 6 | His | AIB | His | Gly | Thr | Phe | Thr | Ser | Asp | Tyr |
| 7 | His | AIB | His | Gly | Thr | Phe | Thr | Ser | Asp | Tyr |
| 8 | His | AIB | His | Gly | Thr | Phe | Thr | Ser | Asp | Tyr |
| 9 | His | AIB | His | Gly | Thr | Phe | Thr | Ser | Asp | Tyr |
| 10 | His | AIB | His | Gly | Thr | Phe | Thr | Ser | Asp | Tyr |
| 11 | His | AIB | His | Gly | Thr | Phe | Thr | Ser | Asp | Tyr |
| 12 | His | AIB | His | Gly | Thr | Phe | Thr | Ser | Asp | Tyr |
| 13 | His | AIB | His | Gly | Thr | Phe | Thr | Ser | Asp | Tyr |
| 14 | His | AIB | His | Gly | Thr | Phe | Thr | Ser | Asp | Tyr |
| 15 | His | AIB | His | Gly | Thr | Phe | Thr | Ser | Asp | Tyr |
| 16 | His | AIB | His | Gly | Thr | Phe | Thr | Ser | Asp | Tyr |
| 17 | His | AIB | His | Gly | Thr | Phe | Thr | Ser | Asp | Tyr |
| 18 | His | AIB | His | Gly | Thr | Phe | Thr | Ser | Asp | Tyr |
| 19 | His | AIB | His | Gly | Thr | Phe | Thr | Ser | Asp | Tyr |
| 20 | His | AIB | His | Gly | Thr | Phe | Thr | Ser | Asp | Tyr |
| 21 | His | AIB | His | Gly | Thr | Phe | Thr | Ser | Asp | Tyr |
| 22 | His | AIB | His | Gly | Thr | Phe | Thr | Ser | Asp | Tyr |
| 23 | His | AIB | His | Gly | Thr | Phe | Thr | Ser | Asp | Tyr |
| 24 | His | AIB | His | Gly | Thr | Phe | Thr | Ser | Asp | Tyr |
| 25 | His | AIB | His | Gly | Thr | Phe | Thr | Ser | Asp | Tyr |
| 26 | His | AIB | His | Gly | Thr | Phe | Thr | Ser | Asp | Tyr |
| 27 | His | AIB | His | Gly | Thr | Phe | Thr | Ser | Asp | Tyr |

Fig. 1

| Example No. | Amino Acid Residue Position |||||||||||
|---|---|---|---|---|---|---|---|---|---|---|
| | 11 | 12 | 13 | 14 | 15 | 16 | 17 | 18 | 19 | 20 |
| 1 | Ser | Arg | Tyr | Leu | Asp | Gln | Arg | Arg | Ala | Gln |
| 2 | Ser | Arg | Tyr | Leu | Asp | Glu | Arg | Arg | Ala | Gln |
| 3 | Ser | Arg | Tyr | Leu | Asp | Gln | Arg | Arg | Ala | Gln |
| 4 | Ser | Arg | Tyr | Leu | Asp | Gln | Arg | Arg | Ala | Gln |
| 5 | Ser | Arg | Tyr | Leu | Asp | Glu | Arg | Arg | Ala | Gln |
| 6 | Ser | Arg | Tyr | Leu | Asp | Gln | Arg | Arg | Ala | Gln |
| 7 | Ser | Arg | Tyr | Leu | Asp | Glu | Arg | Arg | Ala | Gln |
| 8 | Ser | Arg | Tyr | Leu | Asp | Glu | Arg | Arg | Ala | Gln |
| 9 | Ser | Lys | Tyr | Leu | Asp | Glu | Lys | Arg | Ala | His |
| 10 | Ser | Arg | Tyr | Leu | Asp | Gln | Arg | Arg | Ala | Gln |
| 11 | Ser | Arg | Tyr | Leu | Asp | Glu | Arg | Arg | Ala | Gln |
| 12 | Ser | Arg | Tyr | Leu | Asp | Glu | Arg | Arg | Ala | Gln |
| 13 | Ser | Arg | Tyr | Leu | Asp | Gln | Arg | Arg | Ala | Gln |
| 14 | Ser | Arg | Tyr | Leu | Asp | Gln | Arg | Arg | Ala | Gln |
| 15 | Ser | Arg | Tyr | Leu | Asp | Gln | Lys | Arg | Ala | Gln |
| 16 | Ser | Arg | Tyr | Leu | Asp | Gln | Lys | Arg | Ala | Gln |
| 17 | Ser | Arg | Tyr | Leu | Asp | Glu | Arg | Arg | Ala | Gln |
| 18 | Ser | Arg | Tyr | Leu | Asp | Glu | Arg | Arg | Ala | Gln |
| 19 | Ser | Arg | Tyr | Leu | Asp | His | Lys | Arg | Ala | Gln |
| 20 | Ser | Arg | Tyr | Leu | Asp | Gln | Lys | Arg | Ala | Gln |
| 21 | Ser | Arg | Tyr | Leu | Asp | Gln | Lys | Arg | Ala | Gln |
| 22 | Ser | Arg | Tyr | Leu | Asp | Glu | Arg | Arg | Ala | Gln |
| 23 | Ser | Arg | Tyr | Leu | Asp | Glu | Arg | Arg | Ala | Gln |
| 24 | Ser | Lys | Tyr | Leu | Asp | Ala | Lys | Arg | Ala | Gln |
| 25 | Ser | Arg | Tyr | Leu | Asp | Glu | Lys | Arg | Ala | Gln |
| 26 | Ser | Arg | Tyr | Leu | Asp | Gln | Arg | Arg | Ala | Gln |
| 27 | Ser | Arg | Tyr | Leu | Asp | Glu | Arg | Arg | Ala | Gln |

Fig. 1 continued

| Example No. | Amino Acid Residue Position | | | | | | | | | |
|---|---|---|---|---|---|---|---|---|---|---|
| | 21 | 22 | 23 | 24 | 25 | 26 | 27 | 28 | 29 | 30 |
| 1 | Glu | Phe | Ile | Glu | Trp | Leu | Leu | Ala | Thr | His |
| 2 | Glu | Phe | Ile | Glu | Trp | Leu | Leu | Thr | Gly | His |
| 3 | Glu | Phe | Ile | Glu | Trp | Leu | Leu | His | Thr | His |
| 4 | Glu | Phe | Ile | Glu | Trp | Leu | Leu | Ala | Thr | His |
| 5 | Glu | Phe | Ile | Glu | Trp | Leu | Leu | His | Gly | His |
| 6 | Glu | Phe | Ile | Glu | Trp | Leu | Leu | His | Thr | His |
| 7 | Glu | Phe | Ile | Glu | Trp | Leu | Leu | Thr | Gly | His |
| 8 | Glu | Phe | Ile | Glu | Trp | Leu | Leu | His | Gly | His |
| 9 | Glu | Phe | Ile | Glu | Trp | Leu | Leu | His | Gly | His |
| 10 | Glu | Phe | Ile | Glu | Trp | Leu | Leu | Thr | Gly | His |
| 11 | Glu | Phe | Ile | Glu | Trp | Leu | Leu | Thr | Gly | His |
| 12 | Glu | Phe | Ile | Glu | Trp | Leu | Leu | Thr | Gly | His |
| 13 | Glu | Phe | Ile | Glu | Trp | Leu | Leu | His | Thr | His |
| 14 | Glu | Phe | Ile | Glu | Trp | Leu | Leu | Asn | Thr | His |
| 15 | Glu | Phe | Ile | Glu | Trp | Leu | Leu | His | Gly | His |
| 16 | Glu | Phe | Ile | Glu | Trp | Leu | Leu | Ala | Thr | His |
| 17 | Glu | Phe | Ile | Glu | Trp | Leu | Leu | His | Thr | His |
| 18 | Glu | Phe | Ile | Glu | Trp | Leu | Leu | Ala | Gly | His |
| 19 | Glu | Phe | Ile | Glu | Trp | Leu | Leu | His | Gly | His |
| 20 | Glu | Phe | Ile | Glu | Trp | Leu | Leu | Leu | Thr | His |
| 21 | Glu | Phe | Ile | Glu | Trp | Leu | Leu | Leu | Thr | His |
| 22 | Glu | Phe | Ile | Glu | Trp | Leu | Leu | Thr | Gly | His |
| 23 | Glu | Phe | Ile | Glu | Trp | Leu | Leu | Thr | Gly | His |
| 24 | Glu | Phe | Ile | Glu | Trp | Leu | Leu | Gln | Ser | His |
| 25 | Glu | Phe | Ile | Glu | Trp | Leu | Leu | Leu | Thr | His |
| 26 | Glu | Phe | Ile | Glu | Trp | Leu | Leu | His | Thr | His |
| 27 | Glu | Phe | Ile | Glu | Trp | Leu | Leu | Asn | Thr | His |

Fig. 1 continued

| Example No. | Amino Acid Residue Position | | | | | | | | | |
|---|---|---|---|---|---|---|---|---|---|---|
| | 31 | 32 | 33 | 34 | 35 | 36 | 37 | 38 | 39 | 40 |
| 1 | His | His | His | His | Pro | Ser | NH2 | | | |
| 2 | His | His | His | His | Pro | Ser | | | | |
| 3 | His | His | His | His | Pro | Thr | | | | |
| 4 | His | His | His | His | Leu | Ser | | | | |
| 5 | His | His | His | His | Gly | Leu | Ser | | | |
| 6 | His | His | His | His | Thr | Thr | | | | |
| 7 | His | His | His | His | Pro | Ser | Gly | Trp | | |
| 8 | His | His | His | His | Ser | Val | Pro | Pro | Pro | NH2 |
| 9 | His | His | His | His | Ser | Trp | | | | |
| 10 | His | His | His | His | Gln | Gly | Trp | | | |
| 11 | His | His | His | His | Gln | Gly | Trp | | | |
| 12 | His | His | His | His | Gln | Trp | | | | |
| 13 | His | His | His | His | Pro | Ser | NH2 | | | |
| 14 | His | His | His | His | Ser | Val | | | | |
| 15 | His | His | His | His | Gly | Leu | Ser | | | |
| 16 | His | His | His | His | Pro | Ser | | | | |
| 17 | His | His | His | His | Gly | Pro | Thr | | | |
| 18 | His | His | His | His | Val | Ser | Pro | Pro | Pro | Trp |
| 19 | His | His | His | His | Pro | Ser | | | | |
| 20 | His | His | His | His | Pro | Ser | | | | |
| 21 | His | His | His | His | Ser | | | | | |
| 22 | His | His | His | His | Gly | Gln | Trp | | | |
| 23 | His | His | His | His | Ser | Val | Pro | Pro | Pro | Trp |
| 24 | His | His | His | His | Pro | Ser | Trp | | | |
| 25 | His | His | His | His | Val | | | | | |
| 26 | His | His | His | His | Gly | Leu | Ser | | | |
| 27 | His | His | His | His | Ser | Val | | | | |

Fig. 1 continued

| Peptide | Average ratio to GLP-1 ± SEM | Average ratio to glucagon ± SEM |
|---|---|---|
| 3 | 1.6 ± 0.13 | 0.5 ± 0.06 |
| 4 | 4.2 ± 0.33 | 0.9 ± 0.06 |
| 6 | 2.5 ± 0.16 | 0.8 ± 0.08 |
| 10 | 2.0 ± 0.20 | 0.7 ± 0.06 |
| 11 | 1.8 ± 0.06 | 1.0 ± 0.08 |
| 12 | 2.3 ± 0.18 | 1.5 ± 0.16 |
| 14 | 2.9 ± 0.24 | 1.1 ± 0.08 |
| 15 | 2.2 ± 0.11 | 1.0 ± 0.06 |
| 18 | 2.9 ± 0.77 | 0.9 ± 0.12 |
| 19 | 2.6 ± 0.27 | 1.0 ± 0.14 |
| 21 | 2.7 ± 0.44 | 0.6 ± 0.10 |
| 23 | 2.3 ± 0.28 | 0.8 ± 0.08 |
| 24 | 3.3 ± 0.19 | 0.8 ± 0.06 |
| 25 | 3.7 ± 0.46 | 1 ± 0.16 |

Fig. 2

| Peptide | $E_{max}$ (relative to GLP-1) | $EC_{50}$ (relative to GLP-1) ± SD (nM) |
|---|---|---|
| 1 | 1.4 | 3.3 ± 0.3 |
| 2 | 1.6 | 2.1 ± 0.2 |
| 3 | 1.2 | 1.1 ± 0.1 |
| 4 | 1.1 | 7.0 ± 0.3 |
| 5 | 1.4 | 1.0 ± 0.2 |
| 6 | 1.0 | 7.3 ± 0.2 |
| 7 | 1.2 | 3.8 ± 0.5 |
| 8 | 1.2 | 2.7 |
| 9 | 1.4 | 0.9 ± 0.3 |
| 10 | 1.2 | 2.4 ± 0.0 |
| 11 | 10.3 | 5.1 ± 0.4 |
| 12 | 1.4 | 2.0 ± 0.2 |
| 13 | 1.3 | 5.4 ± 0.2 |
| 14 | 1.3 | 6.2 ± 0.1 |
| 15 | 1.3 | 1.3 ± 0.4 |
| 16 | 1.0 | 1.8 ± 0.1 |
| 17 | 1.3 | 1.4 ± 0.2 |
| 18 | 1.0 | 1.5 ± 0.2 |
| 23 | 1.4 | 5.4 ± 0.1 |
| 24 | 1.7 | 1.5 ± 0.3 |
| 25 | 1.7 | 5.48 ± 0.01 |

Fig. 5

SEQUENCE LISTING

```
<160> NUMBER OF SEQ ID NOS: 55

<210> SEQ ID NO 1
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (36)..(36)
<223> OTHER INFORMATION: AMIDATION of Ser residue to give Ser-NH2

<400> SEQUENCE: 1

His Xaa His Gly Thr Phe Thr Ser Asp Tyr Ser Arg Tyr Leu Asp Gln
1               5                   10                  15

Arg Arg Ala Gln Glu Phe Ile Glu Trp Leu Leu Ala Thr His His His
            20                  25                  30

His His Pro Ser
        35

<210> SEQ ID NO 2
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 2

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Thr Gly His His His
            20                  25                  30

His His Pro Ser
        35

<210> SEQ ID NO 3
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 3

His Xaa His Gly Thr Phe Thr Ser Asp Tyr Ser Arg Tyr Leu Asp Gln
1               5                   10                  15
```

Arg Arg Ala Gln Glu Phe Ile Glu Trp Leu Leu His Thr His His
            20                  25                  30

His His Pro Thr
        35

<210> SEQ ID NO 4
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 4

His Xaa His Gly Thr Phe Thr Ser Asp Tyr Ser Arg Tyr Leu Asp Gln
1               5                   10                  15

Arg Arg Ala Gln Glu Phe Ile Glu Trp Leu Leu Ala Thr His His His
            20                  25                  30

His His Leu Ser
        35

<210> SEQ ID NO 5
<211> LENGTH: 37
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 5

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu His Gly His His His
            20                  25                  30

His His Gly Leu Ser
        35

<210> SEQ ID NO 6
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 6

His Xaa His Gly Thr Phe Thr Ser Asp Tyr Ser Arg Tyr Leu Asp Gln
1               5                   10                  15

Arg Arg Ala Gln Glu Phe Ile Glu Trp Leu Leu His Thr His His His
            20                  25                  30

His His Thr Thr
        35

<210> SEQ ID NO 7
<211> LENGTH: 38
<212> TYPE: PRT

```
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 7

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Thr Gly His His His
            20                  25                  30

His His Pro Ser Gly Trp
        35

<210> SEQ ID NO 8
<211> LENGTH: 39
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (39)..(39)
<223> OTHER INFORMATION: AMIDATION of Pro residue to give Pro-NH2

<400> SEQUENCE: 8

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu His Gly His His His
            20                  25                  30

His His Ser Val Pro Pro Pro
        35

<210> SEQ ID NO 9
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 9

His Xaa His Gly Thr Phe Thr Ser Asp Tyr Ser Lys Tyr Leu Asp Glu
1               5                   10                  15

Lys Arg Ala His Glu Phe Ile Glu Trp Leu Leu His Gly His His His
            20                  25                  30

His His Ser Trp
        35

<210> SEQ ID NO 10
<211> LENGTH: 37
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
```

```
<223> OTHER INFORMATION: Aib

<400> SEQUENCE: 10

His Xaa His Gly Thr Phe Thr Ser Asp Tyr Ser Arg Tyr Leu Asp Gln
1               5                   10                  15

Arg Arg Ala Gln Glu Phe Ile Glu Trp Leu Leu Thr Gly His His His
            20                  25                  30

His His Gln Gly Trp
        35

<210> SEQ ID NO 11
<211> LENGTH: 37
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 11

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Thr Gly His His His
            20                  25                  30

His His Gln Gly Trp
        35

<210> SEQ ID NO 12
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 12

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Thr Gly His His His
            20                  25                  30

His His Gln Trp
        35

<210> SEQ ID NO 13
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (36)..(36)
<223> OTHER INFORMATION: AMIDATION of Ser residue to give Ser-NH2

<400> SEQUENCE: 13

His Xaa His Gly Thr Phe Thr Ser Asp Tyr Ser Arg Tyr Leu Asp Gln
1               5                   10                  15
```

Arg Arg Ala Gln Glu Phe Ile Glu Trp Leu Leu His Thr His His
            20                  25                  30

His His Pro Ser
        35

<210> SEQ ID NO 14
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 14

His Xaa His Gly Thr Phe Thr Ser Asp Tyr Ser Arg Tyr Leu Asp Gln
1               5                   10                  15

Arg Arg Ala Gln Glu Phe Ile Glu Trp Leu Leu Asn Thr His His His
            20                  25                  30

His His Ser Val
        35

<210> SEQ ID NO 15
<211> LENGTH: 37
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 15

His Xaa His Gly Thr Phe Thr Ser Asp Tyr Ser Arg Tyr Leu Asp Gln
1               5                   10                  15

Lys Arg Ala Gln Glu Phe Ile Glu Trp Leu Leu His Gly His His His
            20                  25                  30

His His Gly Leu Ser
        35

<210> SEQ ID NO 16
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 16

His Xaa His Gly Thr Phe Thr Ser Asp Tyr Ser Arg Tyr Leu Asp Gln
1               5                   10                  15

Lys Arg Ala Gln Glu Phe Ile Glu Trp Leu Leu Ala Thr His His His
            20                  25                  30

His His Pro Ser
        35

<210> SEQ ID NO 17
<211> LENGTH: 37

```
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 17

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu His Thr His His His
            20                  25                  30

His His Gly Pro Thr
        35

<210> SEQ ID NO 18
<211> LENGTH: 40
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 18

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Ala Gly His His His
            20                  25                  30

His His Val Ser Pro Pro Pro Trp
        35                  40

<210> SEQ ID NO 19
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 19

His Xaa His Gly Thr Phe Thr Ser Asp Tyr Ser Arg Tyr Leu Asp His
1               5                   10                  15

Lys Arg Ala Gln Glu Phe Ile Glu Trp Leu Leu His Gly His His His
            20                  25                  30

His His Pro Ser
        35

<210> SEQ ID NO 20
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 20
```

```
His Xaa His Gly Thr Phe Thr Ser Asp Tyr Ser Arg Tyr Leu Asp Gln
1               5                   10                  15

Lys Arg Ala Gln Glu Phe Ile Glu Trp Leu Leu Leu Thr His His His
            20                  25                  30

His His Pro Ser
        35

<210> SEQ ID NO 21
<211> LENGTH: 35
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 21

His Xaa His Gly Thr Phe Thr Ser Asp Tyr Ser Arg Tyr Leu Asp Gln
1               5                   10                  15

Lys Arg Ala Gln Glu Phe Ile Glu Trp Leu Leu Leu Thr His His His
            20                  25                  30

His His Ser
        35

<210> SEQ ID NO 22
<211> LENGTH: 37
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 22

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Thr Gly His His His
            20                  25                  30

His His Gly Gln Trp
        35

<210> SEQ ID NO 23
<211> LENGTH: 40
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 23

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Thr Gly His His His
            20                  25                  30

His His Ser Val Pro Pro Trp
        35                  40
```

```
<210> SEQ ID NO 24
<211> LENGTH: 37
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 24

His Xaa His Gly Thr Phe Thr Ser Asp Tyr Ser Lys Tyr Leu Asp Ala
1               5                   10                  15

Lys Arg Ala Gln Glu Phe Ile Glu Trp Leu Leu Gln Ser His His His
            20                  25                  30

His His Pro Ser Trp
        35

<210> SEQ ID NO 25
<211> LENGTH: 35
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 25

His Xaa His Gly Thr Phe Thr Ser Asp Tyr Ser Arg Tyr Leu Asp Glu
1               5                   10                  15

Lys Arg Ala Gln Glu Phe Ile Glu Trp Leu Leu Leu Thr His His His
            20                  25                  30

His His Val
        35

<210> SEQ ID NO 26
<211> LENGTH: 37
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
<223> OTHER INFORMATION: Aib

<400> SEQUENCE: 26

His Xaa His Gly Thr Phe Thr Ser Asp Tyr Ser Arg Tyr Leu Asp Gln
1               5                   10                  15

Arg Arg Ala Gln Glu Phe Ile Glu Trp Leu Leu His Thr His His His
            20                  25                  30

His His Gly Leu Ser
        35

<210> SEQ ID NO 27
<211> LENGTH: 36
<212> TYPE: PRT
<213> ORGANISM: Artificial Sequence
<220> FEATURE:
<223> OTHER INFORMATION: peptide hormone analogues
<220> FEATURE:
<221> NAME/KEY: MOD_RES
<222> LOCATION: (2)..(2)
```

```
<223> OTHER INFORMATION: Aib

<400> SEQUENCE: 27

His Xaa His Gly Thr Phe Thr Ser Asp Tyr Ser Arg Tyr Leu Asp Glu
1               5                   10                  15

Arg Arg Ala Gln Glu Phe Ile Glu Trp Leu Leu Asn Thr His His His
            20                  25                  30

His His Ser Val
        35

<210> SEQ ID NO 28
<211> LENGTH: 29
<212> TYPE: PRT
<213> ORGANISM: Artificial Sequence
<220> FEATURE:
<223> OTHER INFORMATION: peptide hormone analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(12)
<223> OTHER INFORMATION: The residue at this position is Lys or Arg
<220> FEATURE:
<221> NAME/KEY: MOD_RES
<222> LOCATION: (16)..(16)
<223> OTHER INFORMATION: The residue at this position is Ala, Gln, Glu,
      His or Thr
<220> FEATURE:
<221> NAME/KEY: MOD_RES
<222> LOCATION: (17)..(17)
<223> OTHER INFORMATION: The residue at this position is Lys or Arg
<220> FEATURE:
<221> NAME/KEY: MOD_RES
<222> LOCATION: (20)..(20)
<223> OTHER INFORMATION: The residue at this position is Gln or His
<220> FEATURE:
<221> NAME/KEY: MOD_RES
<222> LOCATION: (21)..(21)
<223> OTHER INFORMATION: The residue at this position is Glu or Asp
<220> FEATURE:
<221> NAME/KEY: MOD_RES
<222> LOCATION: (28)..(28)
<223> OTHER INFORMATION: The residue at this position is Gln, Asn, His,
      Ala, Thr, Leu, Ser or Ile
<220> FEATURE:
<221> NAME/KEY: MOD_RES
<222> LOCATION: (29)..(29)
<223> OTHER INFORMATION: The residue at this position is Ser, Thr or Gly

<400> SEQUENCE: 28

His Xaa His Gly Thr Phe Thr Ser Asp Tyr Ser Xaa Tyr Leu Asp Xaa
1               5                   10                  15

Xaa Arg Ala Xaa Xaa Phe Ile Glu Trp Leu Leu Xaa Xaa
            20                  25

<210> SEQ ID NO 29
<211> LENGTH: 5
<212> TYPE: PRT
<213> ORGANISM: Artificial Sequence
<220> FEATURE:
<223> OTHER INFORMATION: Cleavable linker

<400> SEQUENCE: 29

Asp Asp Asp Asp Tyr
1               5

<210> SEQ ID NO 30
<211> LENGTH: 5
```

```
<212> TYPE: PRT
<213> ORGANISM: Artificial Sequence
<220> FEATURE:
<223> OTHER INFORMATION: cleavable linker

<400> SEQUENCE: 30

His Pro Phe His Leu
1               5

<210> SEQ ID NO 31
<211> LENGTH: 31
<212> TYPE: PRT
<213> ORGANISM: Homo sapiens

<400> SEQUENCE: 31

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 32
<211> LENGTH: 31
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: AMIDATION

<400> SEQUENCE: 32

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 33
<211> LENGTH: 29
<212> TYPE: PRT
<213> ORGANISM: Homo sapiens

<400> SEQUENCE: 33

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 34
<211> LENGTH: 37
<212> TYPE: PRT
<213> ORGANISM: Homo sapiens

<400> SEQUENCE: 34

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 35
<211> LENGTH: 5
<212> TYPE: PRT
<213> ORGANISM: Artificial Sequence
<220> FEATURE:
```

```
<223> OTHER INFORMATION: Synthetic sequence
<220> FEATURE:
<223> OTHER INFORMATION: Part of the sequence of V of claim 1

<400> SEQUENCE: 35

His His His His His
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 36

His His His His His Pro Ser Trp
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 37

His His His His His Ser
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 38

His His His His His Val
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 39

His His His His His Ser Val
1               5

<210> SEQ ID NO 40
<211> LENGTH: 7
<212> TYPE: PRT
<213> ORGANISM: Artificial Sequence
<220> FEATURE:
```

```
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 40

His His His His His Ser Trp
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 41

His His His His His Pro Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 42

His His His His His Pro Thr
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 43

His His His His His Leu Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 44

His His His His His Thr Thr
1               5

<210> SEQ ID NO 45
<211> LENGTH: 7
<212> TYPE: PRT
<213> ORGANISM: Artificial Sequence
```

```
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 45

His His His His His Gln Trp
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1
<220> FEATURE:
<221> NAME/KEY: MOD_RES
<222> LOCATION: (7)..(7)
<223> OTHER INFORMATION: AMIDATION of Ser to give Ser-NH2

<400> SEQUENCE: 46

His His His His His Pro Ser
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 47

His His His His His Gln Gly Trp
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 48

His His His His His Gly Gln Trp
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 49

His His His His His Gly Leu Ser
1               5
```

```
<210> SEQ ID NO 50
<211> LENGTH: 8
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 50

His His His His His Gly Pro Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 51

His His His His His Pro Ser Gly Trp
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1
<220> FEATURE:
<221> NAME/KEY: MOD_RES
<222> LOCATION: (10)..(10)
<223> OTHER INFORMATION: AMIDATION of Pro to give Pro-NH2

<400> SEQUENCE: 52

His His His His His Ser Val Pro Pro Pro
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1

<400> SEQUENCE: 53

His His His His His Val Ser Pro Pro Pro Trp
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic sequence
<220> FEATURE:
<223> OTHER INFORMATION: One of several possible identities for V, the
      sub-sequence of the peptide hormone analogue of claim 1
```

```
<400> SEQUENCE: 54

His His His His His Ser Val Pro Pro Pro Trp
1               5                  10

<210> SEQ ID NO 55
<211> LENGTH: 6
<212> TYPE: PRT
<213> ORGANISM: Artificial Sequence
<220> FEATURE:
<223> OTHER INFORMATION: Synthetic sequence
<220> FEATURE:
<223> OTHER INFORMATION: V when a = 1, with Z not included, on page 16
      of the description

<400> SEQUENCE: 55

Gly His His His His His
1               5
```

GLUCAGON-LIKE PEPTIDES

CROSS-REFERENCE TO RELATED APPLICATIONS

This application is the National Stage of International Application No. PCT/GB2018/053512, filed on Dec. 4, 2018, which claims the benefit of and priority to Great Britain Patent Application No. 1720187.2, filed on Dec. 4, 2017, the contents of which are incorporated by reference in their entirety.

SEQUENCE LISTING

The instant application contains a Sequence Listing which has been submitted via EFS-Web and is hereby incorporated by reference in its entirety. Said ASCII copy, created on Sep. 15, 2020, is named 46432US_revisedCRF_sequencelisting.txt, and is 23,334 bytes in size.

FIELD

The present disclosure relates to compounds which are peptide hormone analogues, and which are useful in treating disorders such as diabetes and obesity.

BACKGROUND

According to the National Health and Nutrition Examination Survey (NHANES, 2009-2010), 33.0% of adults in the United States aged 20 and over are overweight, 35.7% are obese, and 6.3% are extremely obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347:358, 2002).

Diabetes is a chronic syndrome of impaired carbohydrate, protein, and fat metabolism owing to insufficient secretion of insulin or to target tissue insulin resistance. It occurs in two major forms: insulin-dependent diabetes mellitus (type 1 diabetes) and non-insulin dependent diabetes mellitus (type 2 diabetes). Diabetes type I, or insulin dependent diabetes mellitus (IDDM) is caused by the destruction of β cells, which results in insufficient levels of endogenous insulin. Diabetes type 2, or non-insulin dependent diabetes, results from a defect in both the body's sensitivity to insulin, and a relative deficiency in insulin production. According to the National Diabetes Statistics Report, 2014 around 28.9 million adults in the United States aged 20 and over have diabetes (2009-2012 National Health and Nutrition Examination Survey estimates applied to 2012 U.S. Census data). In adults 90 to 95% of the diabetes is type 2 diabetes.

There is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia. It has been shown that considerable weight loss can effectively cure type 2 diabetes (Lim et al, Diabetologia June 2011).

Although diet and exercise provide a simple method to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have proven to have serious adverse side effects, and have had to be withdrawn. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example in the upper part of the recommended range, may wish to reduce their weight, to bring it closer to their ideal weight. Thus, a need remains for agents that can be used to effect weight loss in overweight and obese subjects as well as subjects who are of normal weight.

A number of approaches to the development of agents useful in effecting weight loss have involved gastrointestinal peptide hormones and their analogues. For example, derivatives of peptides deriving from the preproglucagon molecule have been proposed for use in treatment of obesity and/or diabetes. Preproglucagon is a precursor peptide of glucagon, as well as other hormones including glucagon-like peptide 1 (GLP-1). Glucagon is released in vivo when blood glucose levels fall low and has the activity of causing the liver to convert stored glycogen into glucose which is released into the bloodstream raising blood glucose levels. GLP-1 is produced in vivo in the intestinal L cell in response to the presence of nutrients in the lumen of the gut. GLP-1 possesses a number of physiological functions including increasing insulin secretion from the pancreas in a glucose-dependent manner, decreasing glucagon secretion from the pancreas, inhibiting gastric emptying and decreasing food intake by increasing satiety. Increased insulin secretion leads to a decrease in circulating glucose concentration.

Examples of research into analogues of such peptides are described in, for example, WO2013/004983 which describes peptide molecules containing sequence from both the GLP-1 and glucagon peptides. WO2015/132599 also discloses peptide hormone analogues, which are derivable from preproglucagon and which are useful in the therapy of disorders such as obesity and diabetes. WO2017/178829 discloses compounds that are analogues of exendin-4, GLP-1 and oxyntomodulin which have a modified ligand bias and therapeutically useful characteristics. Another example is the peptide liraglutide, a GLP-1 agonist which has the sequence of GLP-1$_{(7-37)}$ with an arginine residue substituted for the native lysine at position 34, and with the sidechain of the lysine residue at position 26 being acylated by a hexadecanoyl group. Liraglutide has been developed for use as an injectable drug for the treatment of type II diabetes.

However, despite significant advances, the process of identifying substances useful as drugs remains a complex and, in many cases, unpredictable field. In order to be useful as therapeutic agents, compounds must possess a suitable range of properties. In addition to having good efficacy at the biological target of interest, compounds must have good in vivo pharmacokinetic properties, low toxicity and an acceptable side effect profile. For example, even with commercial agents such as liraglutide, side effects can include nausea and vomiting, and concerns have also been raised with regard to thyroid cancer and pancreatitis.

Thus, there remains a need for further compounds which are useful for the treatment of disorders and diseases such as diabetes and obesity. For example, it would be desirable to identify peptides having beneficial properties such as an improved activity profile, and/or which have reduced side effects.

SUMMARY

In a first aspect there is provided:
a compound having an amino acid sequence of formula (I):

```
His-Aib-His-Gly-Thr-Phe-Thr-Ser-Asp-Tyr-Ser-Xaa12-
Tyr-Leu-Asp-Xaa16-Xaa17-Arg-Ala-Xaa20-Xaa21-Phe-
Ile-Glu-Trp-Leu-Leu-Xaa28-Xaa29-V   (I)
``` wherein
  Xaa12 is Lys or Arg;
  Xaa16 is Ala, Gln, Glu, His or Thr;
  Xaa17 is Lys or Arg;
  Xaa20 is Gln or His;
  Xaa21 is Glu or Asp;
  Xaa28 is Gln, Asn, His, Ala, Thr, Leu, Ser or Ile;
  Xaa29 is Ser, Thr or Gly;
and
V is a sequence consisting of from 5 to 12 amino acid residues, wherein at least 4 of said amino acid residues are His residues, and wherein a carboxylic acid group of the amino acid residue at the C-terminus may optionally be replaced by a —C(O)NH$_2$ group;
or a derivative of the compound; or a salt of the compound or the derivative.
  Preferably,
  Xaa12 is Arg or Lys;
  Xaa16 is Gln, Glu, His or Ala;
  Xaa17 is Arg or Lys;
  Xaa20 is Gln or His;
  Xaa21 is Glu;
  Xaa28 is Asn, His, Ala, Thr, Leu or Gln;
  Xaa29 is Thr, Gly or Ser; and
V is a C-terminal sequence of formula (II):

His-His-His-His-His-Z    (II)

wherein Z is a sequence of from 1 to 6 amino acid residues, and wherein a carboxylic acid group of the amino acid residue at the C-terminus may optionally be replaced by a —C(0)NH$_2$ group.

The compounds, derivatives and salts of the invention comprise specific amino acid residues at certain positions, in particular the compounds comprise an AIB (2-aminoisobutyric acid) residue at position 2 in conjunction with a His (histidine) residue at position 3. It has surprisingly been found that such compounds possess excellent biological properties. For example, the compounds possess a tailored profile with regards to potency properties at the glucagon and GLP-1 receptors. With regard to in vivo properties, administration of example peptides of the invention to rats has been shown to result in increased weight loss. Example compounds have also been shown to achieve these effects without or only minimally reducing the amount of food ingested, indicating that the compounds are particularly effective at improving metabolism. Rodents are not able to vomit, but rodents which are experiencing nausea are likely to be put off from consuming food. The absence of reduction in the levels of food ingested suggests that the rodents did not experience nausea after receiving a compound of the invention. Thus, the absence of reduction in the levels of food ingested in in vivo experiments further supports that the compounds of the invention have an improved side effect profile. In addition, example compounds of the invention have been demonstrated to achieve improved in vitro insulin release effects compared with the commercial peptide liraglutide.

Also provided herein is a composition comprising a compound, derivative or salt as defined herein together with a pharmaceutically acceptable carrier and optionally a further therapeutic agent.

Also provided herein is a compound, derivative or salt as defined herein, or a composition comprising such a compound, derivative or salt and a pharmaceutically acceptable carrier, for use as a medicament, e.g. for use in the prevention or treatment of diabetes, obesity, heart disease, stroke or non-alcoholic fatty liver disease, for increasing the energy expenditure of a subject, improving insulin release in a subject, improving carbohydrate metabolism in a subject, improving the lipid profile of a subject, improving carbohydrate tolerance in a subject, reducing appetite, reducing food intake, reducing calorie intake, and/or for use as a cytoprotective agent.

Also provided herein is a method of treating or preventing a disease or disorder or other non-desired physiological state in a subject comprising administration of a therapeutically effective amount of a compound, derivative or salt as defined herein, or of a composition comprising such a compound, derivative or salt and a pharmaceutically acceptable carrier, e.g. in a method of treating or preventing diabetes, obesity, heart disease, stroke or non-alcoholic fatty liver disease in a subject, for increasing energy expenditure in a subject, improving insulin release in a subject, improving carbohydrate metabolism in a subject, improving the lipid profile of a subject, improving carbohydrate tolerance in a subject, reducing appetite, reducing food intake, reducing calorie intake, and/or providing cytoprotection in a subject.

Also provided herein is a use of a compound, derivative or salt as defined herein for the manufacture of a medicament for the prevention or treatment of diabetes, obesity, heart disease, stroke or non-alcoholic fatty liver disease, increasing the energy expenditure of a subject, improving insulin release in a subject, improving carbohydrate metabolism in a subject, improving the lipid profile of a subject, improving carbohydrate tolerance in a subject, reducing appetite, reducing food intake, reducing calorie intake, and/ or for use as a cytoprotective agent.

Also provided herein is a method of causing weight loss or preventing weight gain in a subject for cosmetic purposes comprising administration of an effective amount of a compound, derivative, salt or composition as defined herein.

BRIEF DESCRIPTION OF THE DRAWINGS

FIG. 1 shows the amino acid sequences of example compounds of the invention. The compounds are presented with the N-terminal residue at the left-hand side of the Table (signified by the column titled "1"). The amino acid sequence for each peptide hormone analogue is set out over four pages. Analogues in the table containing the indication "NH$_2$" next to the C-terminal amino acid residue have a C-terminal amide group (i.e. the C-terminal amino acid residue has a —CONH$_2$ group in place of a C-terminal carboxylic acid).

FIG. 2 is a table showing receptor potency of example compounds at the human GLP-1 and glucagon receptors, overexpressed in CHO cells.

FIG. 5 is a table showing the results of an in vitro assessment of peptide-stimulated insulin secretion, for example compounds.

FIG. 7 shows the total food intake between days 1 to 11 of the study. The results for Example peptides 1 to 19 are shown in FIG. 7a; the results for Example peptides 20 to 24, 26 and 27 are shown in FIG. 7b.

FIG. 8 shows the change in rat body weight between days 1 to 11 of the study. The results for Example peptides 1 to 19 are shown in FIG. 8a; the results for Example peptides 20 to 24, 26 and 27 are shown in FIG. 8b.

DETAILED DESCRIPTION

Sequence listing

Figure 3A:
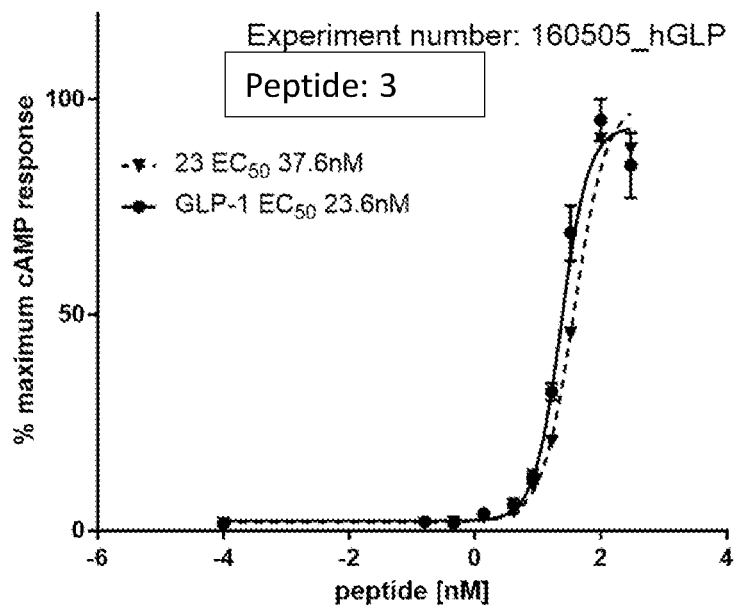
FIG. 3 shows exemplar graphs of peptide-stimulated cAMP production in cells over expressing the human GLP-1 receptor, for example compounds and GLP-1.
Figure 3B:
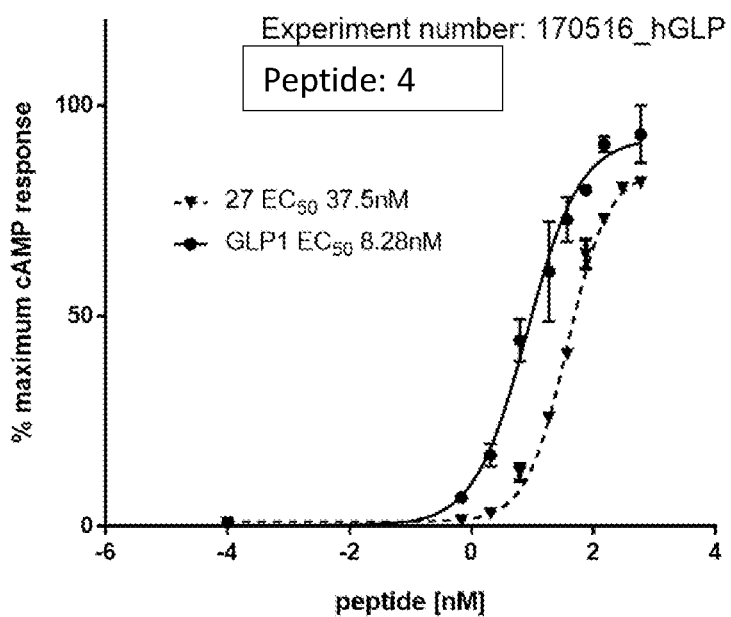
Figure 3C:
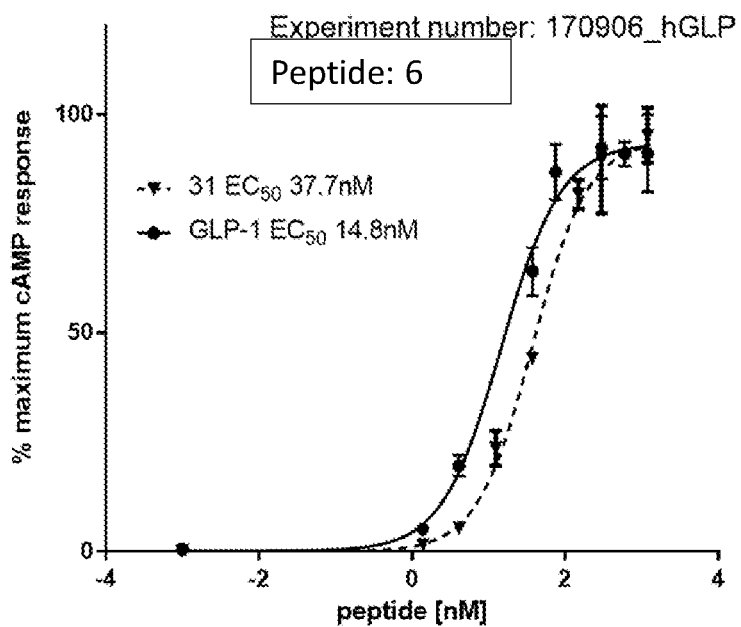
Figure 3D:
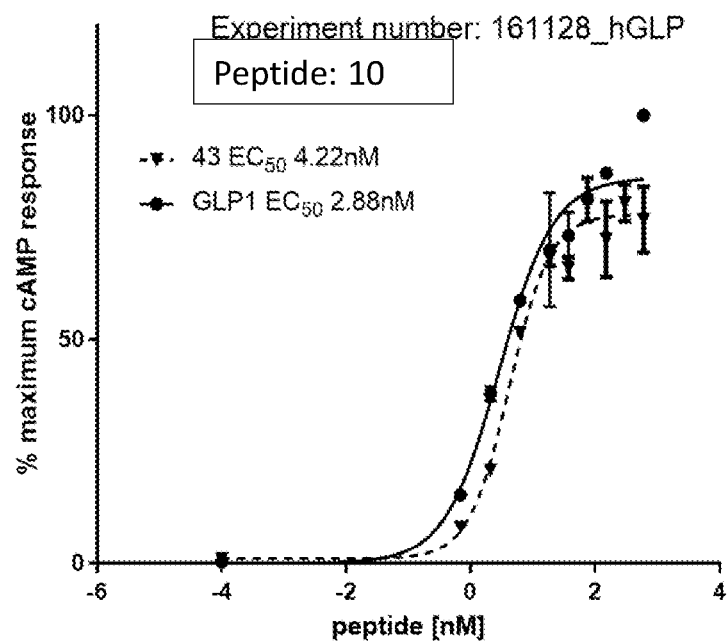
Figure 3E:
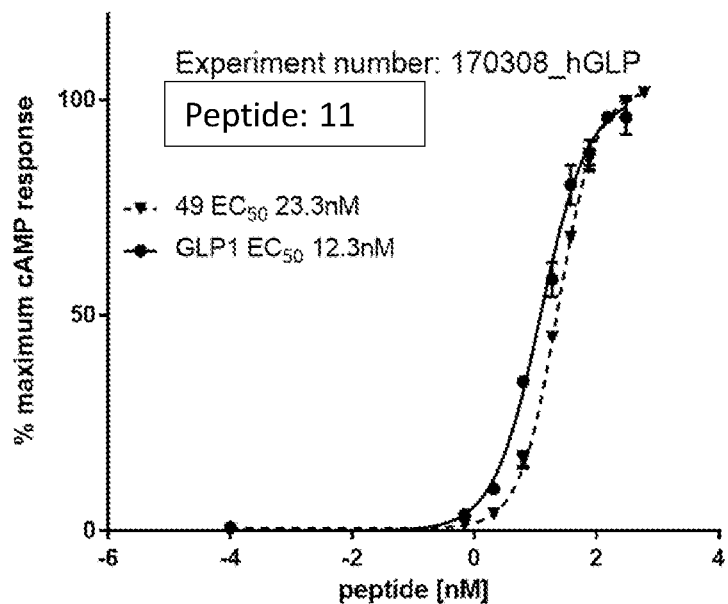
Figure 3F:
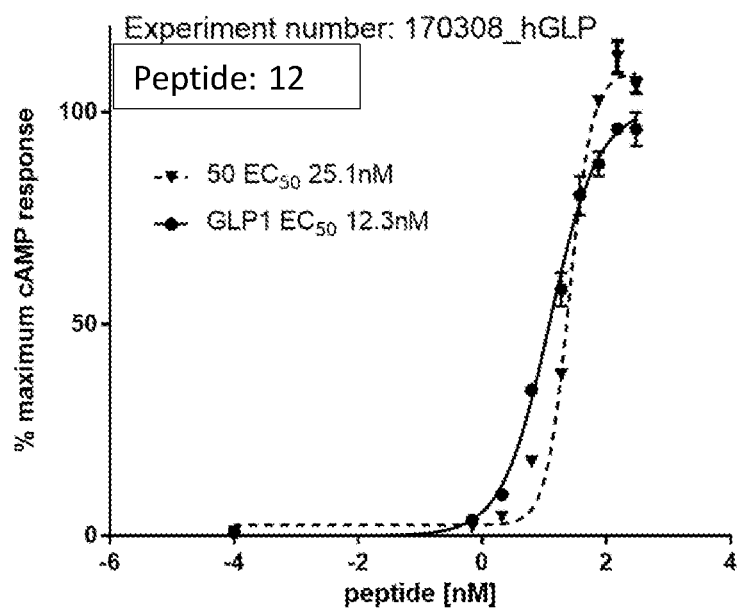
Figure 3G:
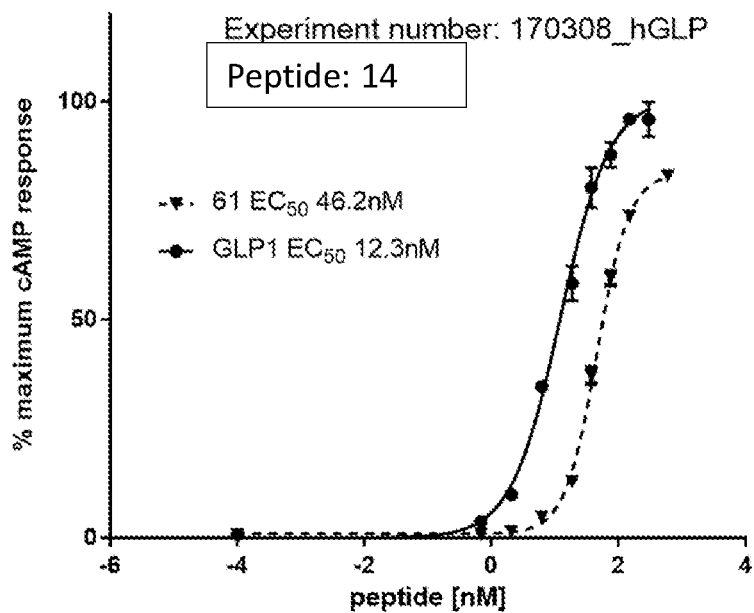
Figure 3H:
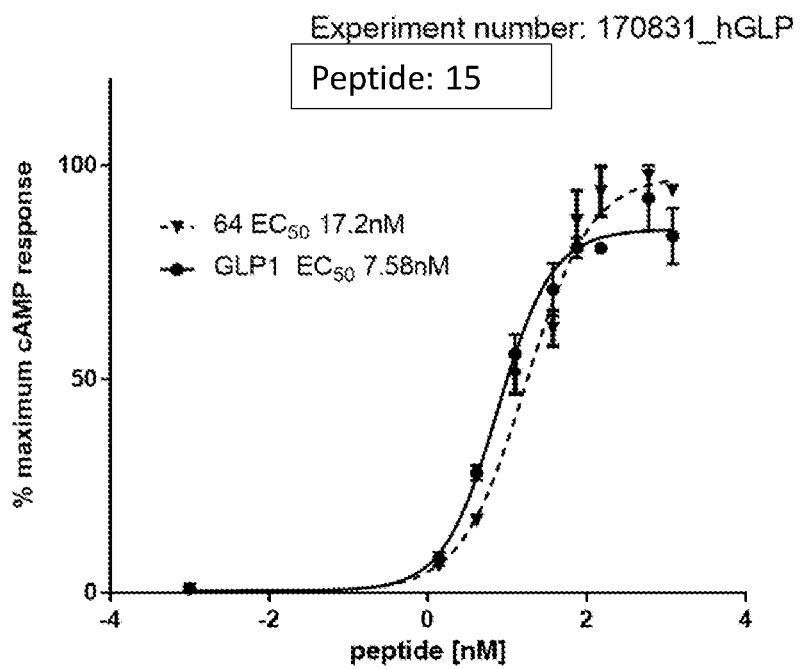
Figure 3I:
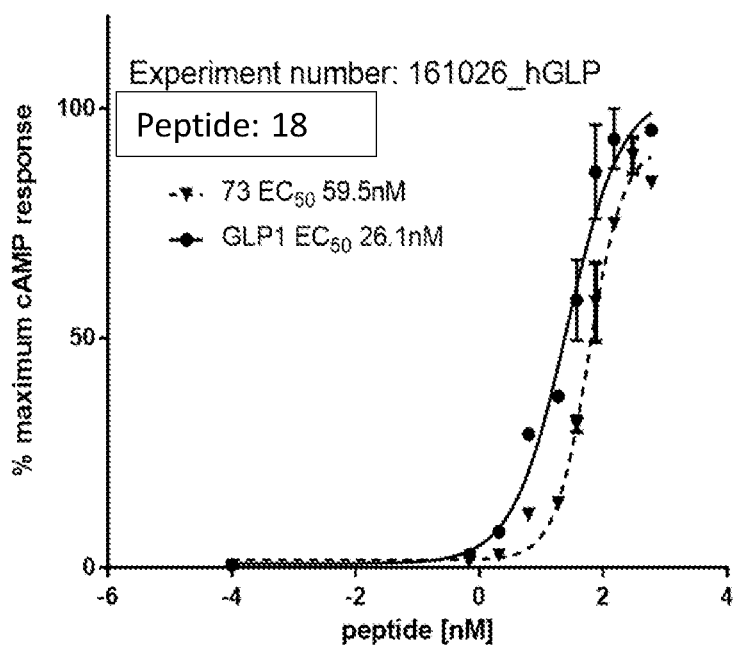
Figure 3J:
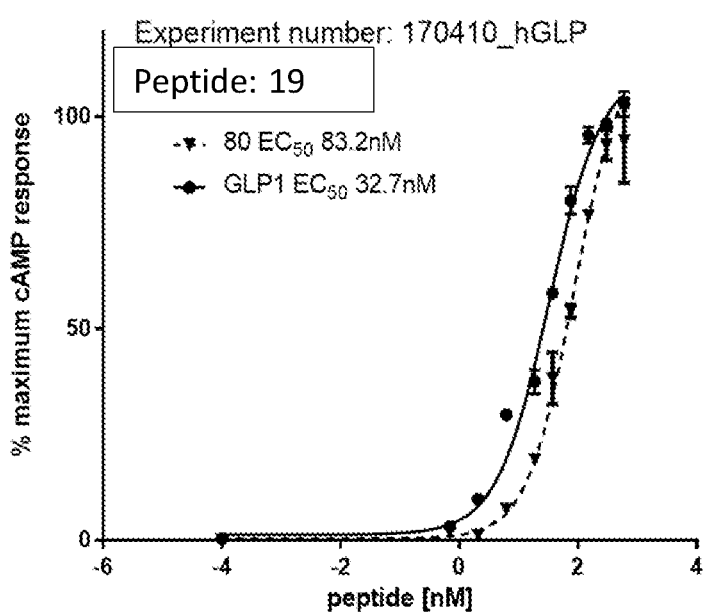
Figure 3K:
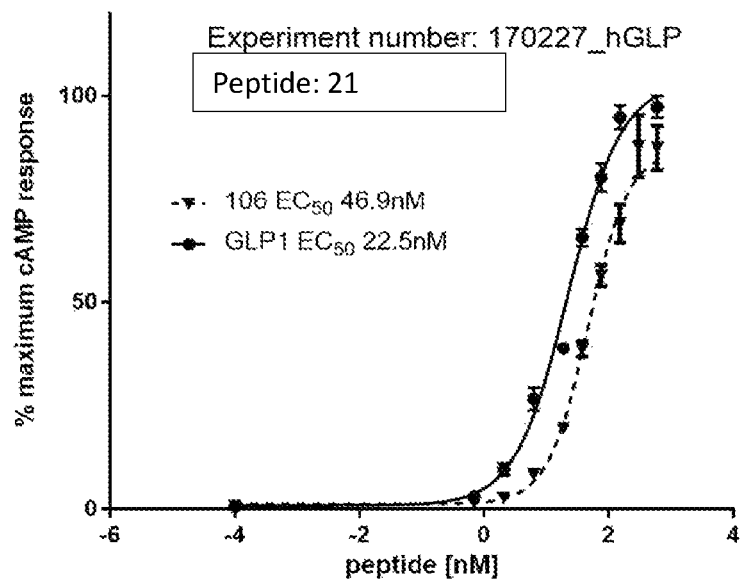
Figure 3L:
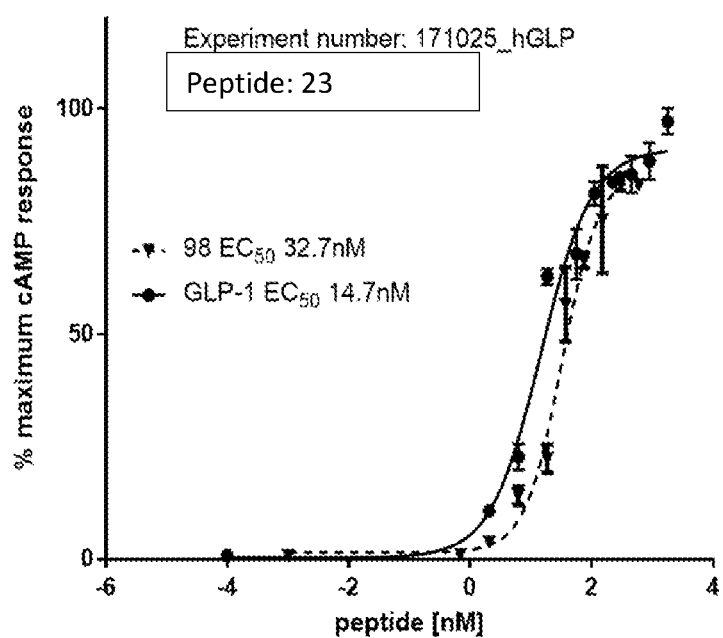
Figure 3M:
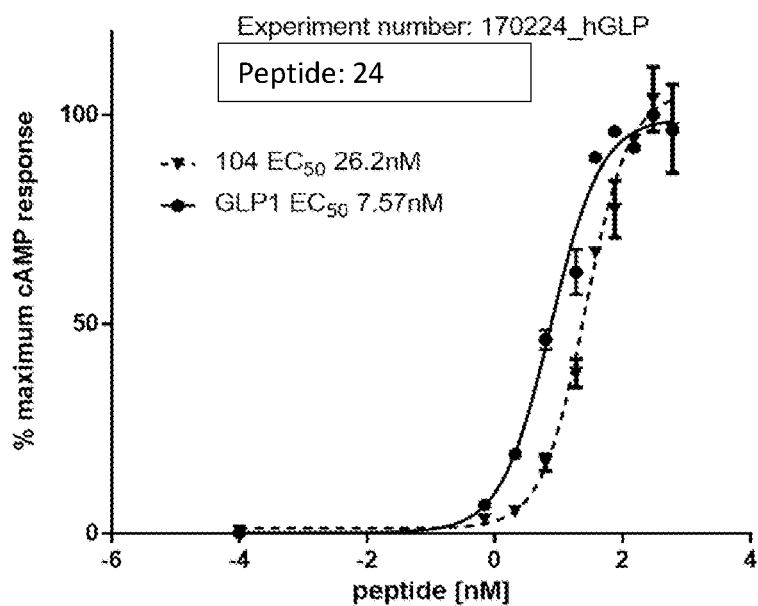
Figure 3N:
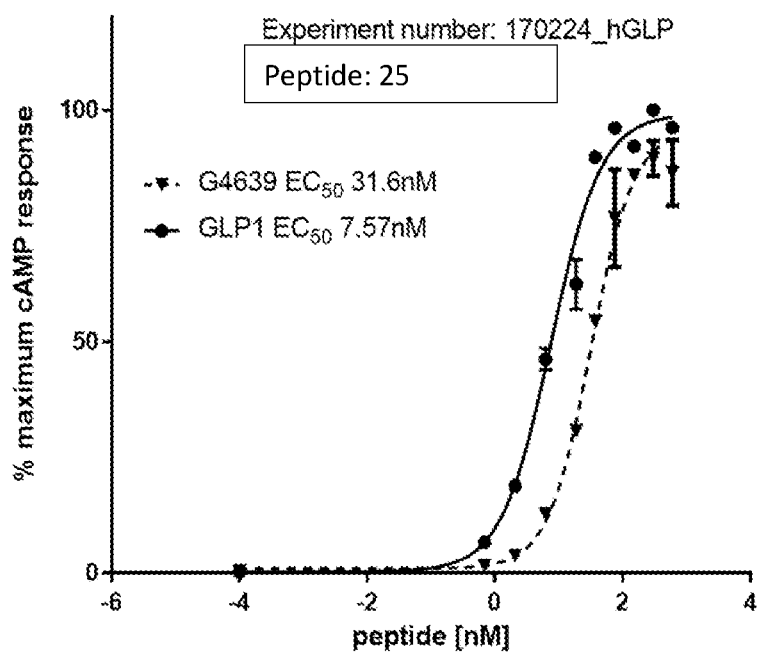
Figure 4A:
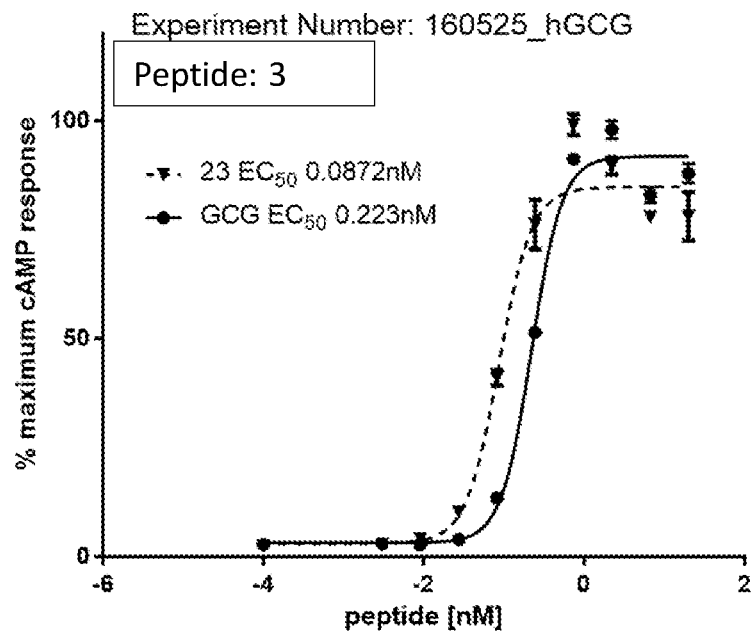
FIG. 4 shows exemplar graphs of peptide-stimulated cAMP production in cells over expressing the human glucagon receptor, for example compounds and glucagon.
Figure 4B:
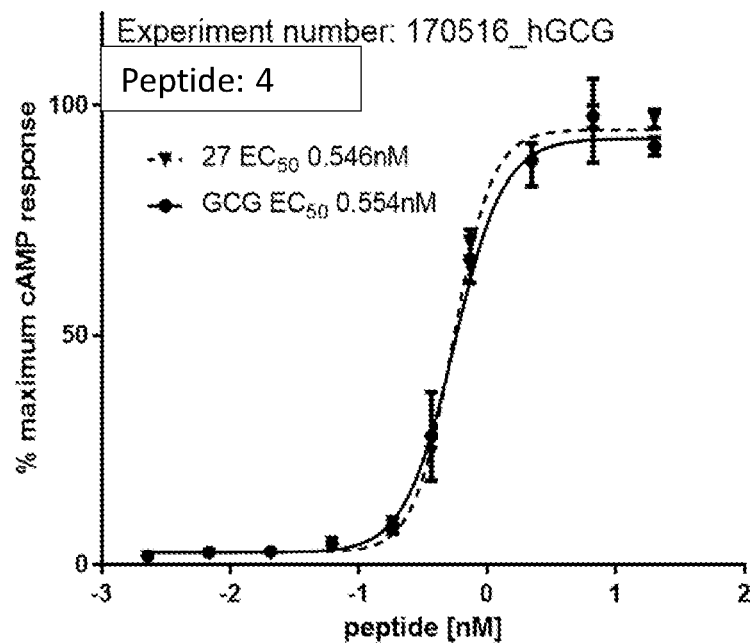
Figure 4C:
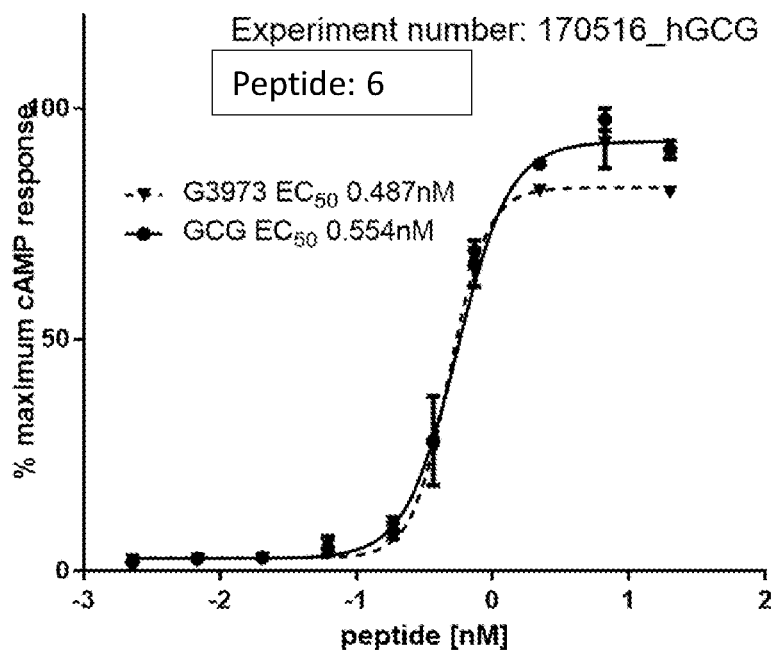
Figure 4D:
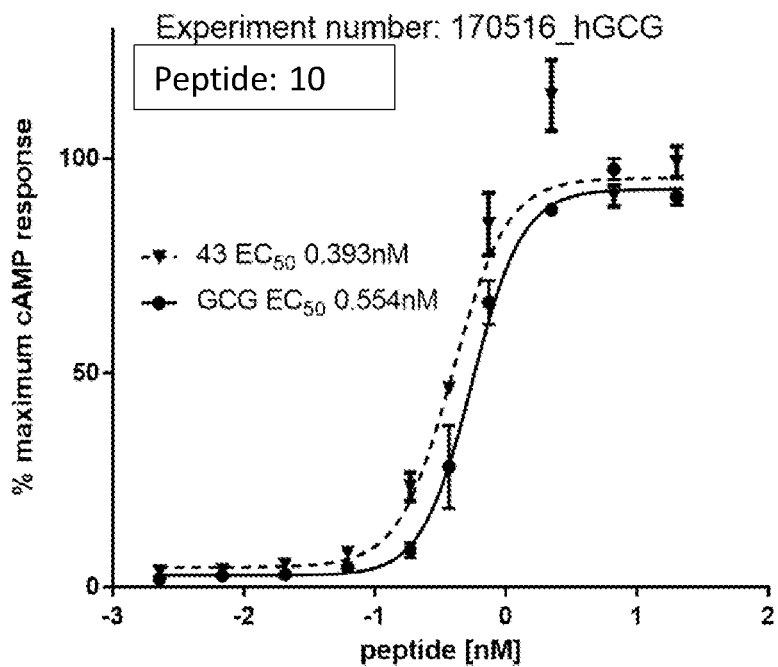
Figure 4E:
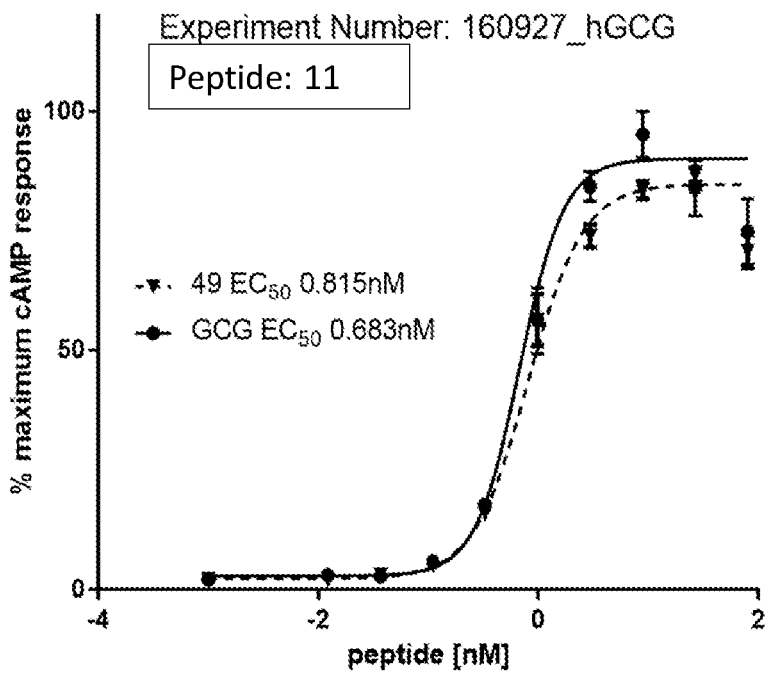
Figure 4F:
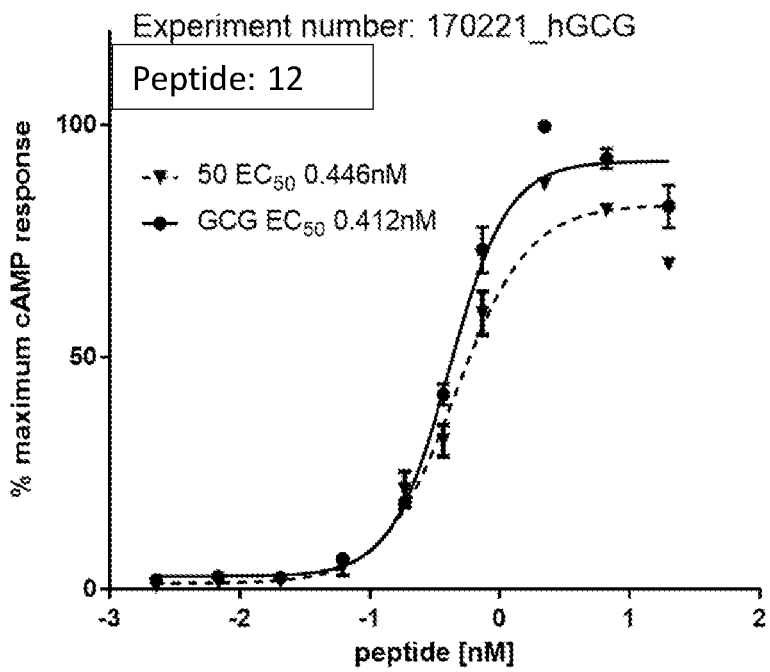
Figure 4G:
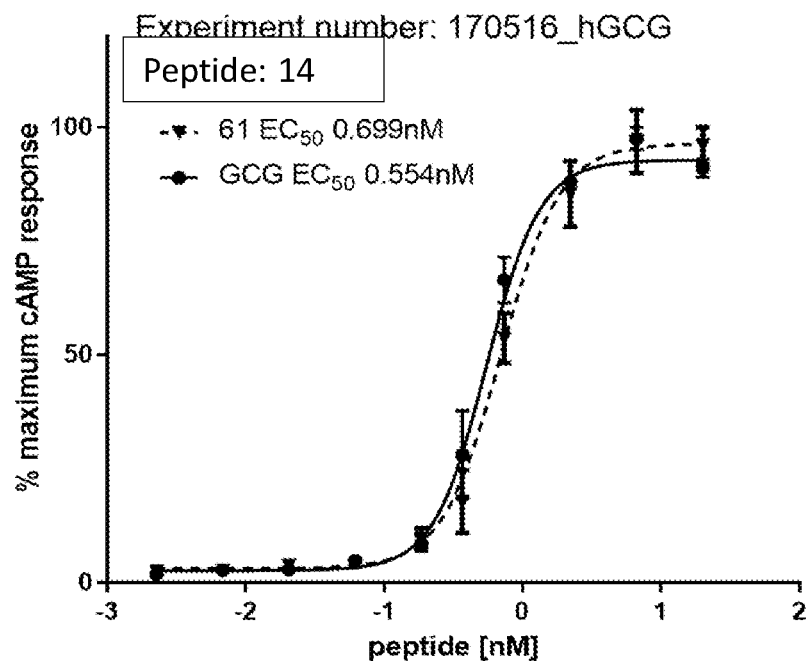
Figure 4H:
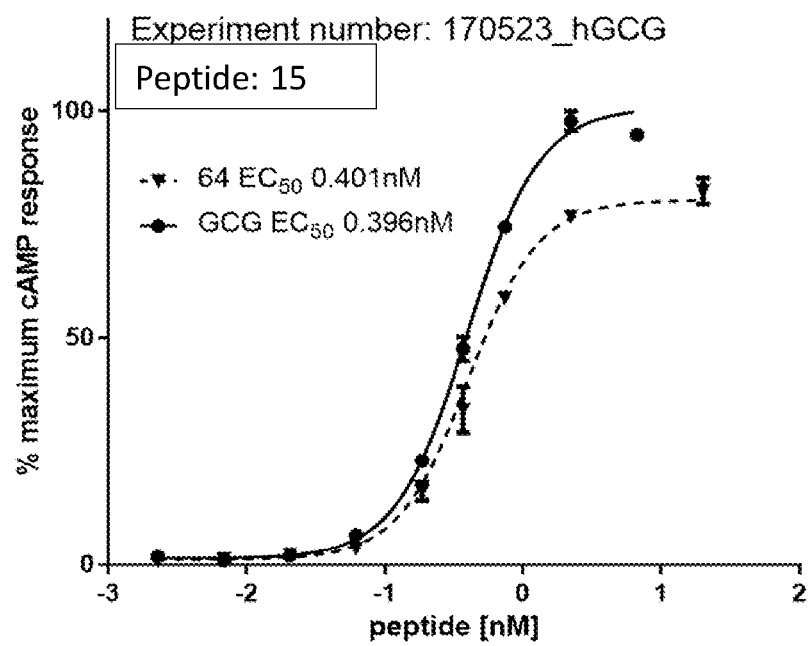
Figure 4I:
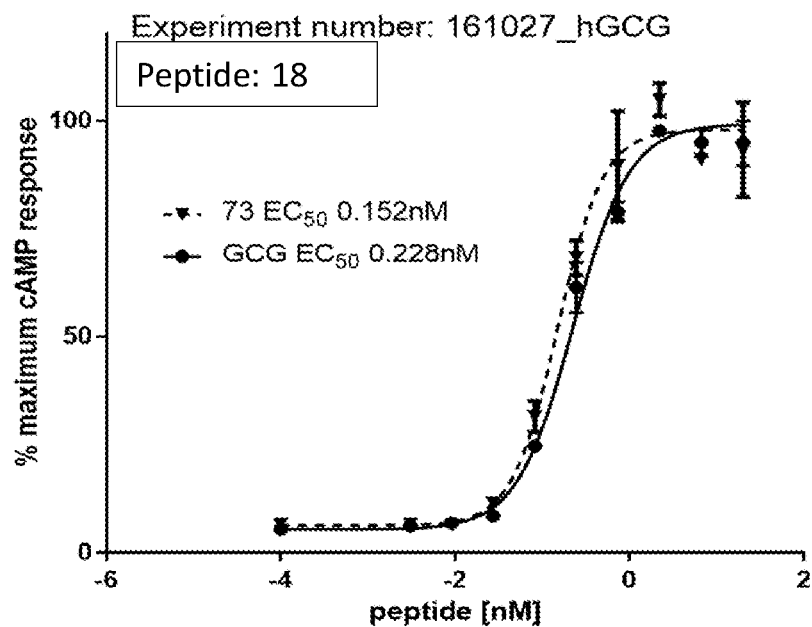
Figure 4J:
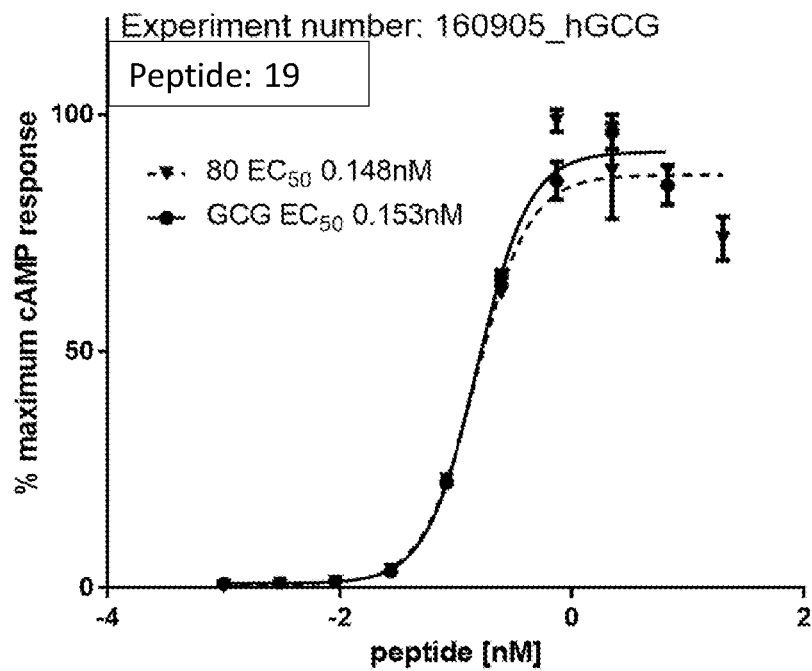
Figure 4K:
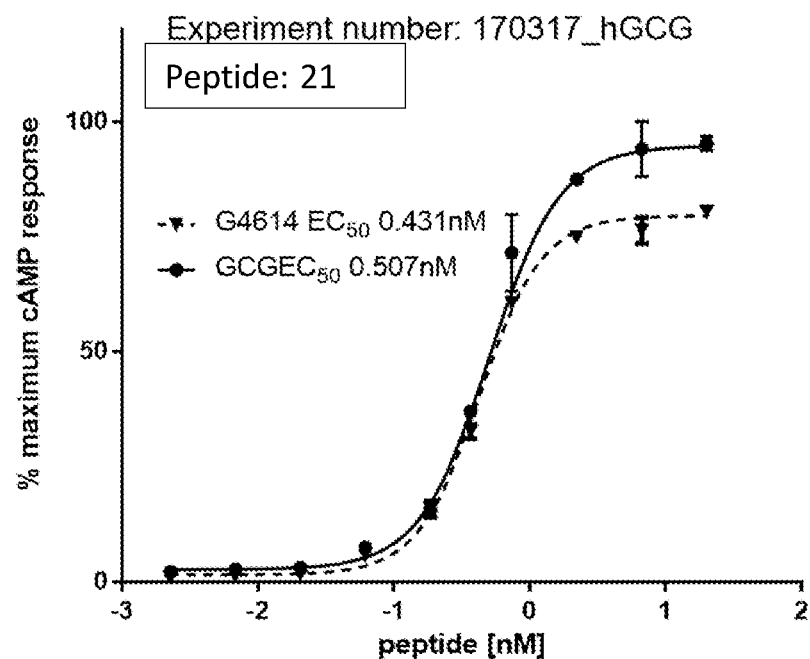
Figure 4L:
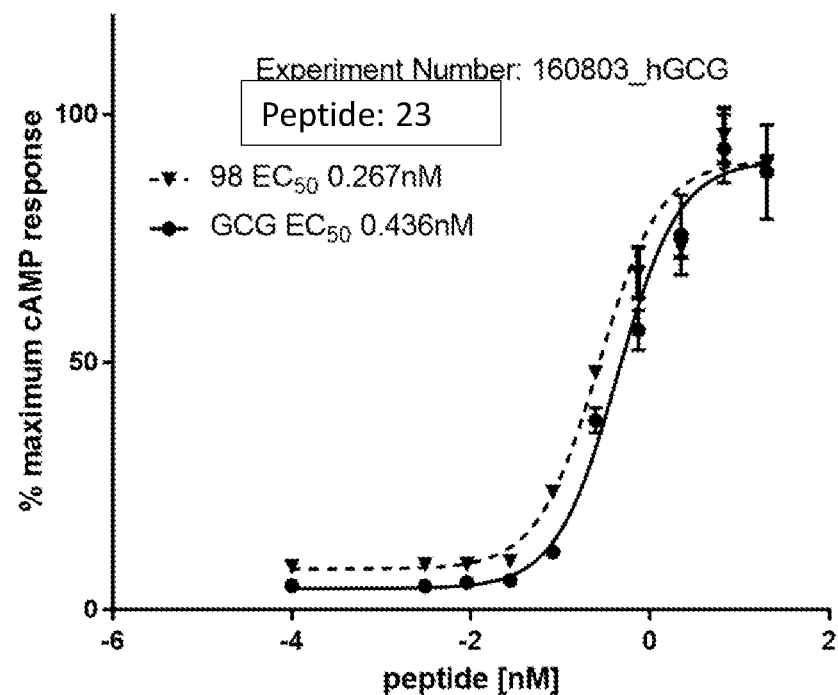
Figure 4M:
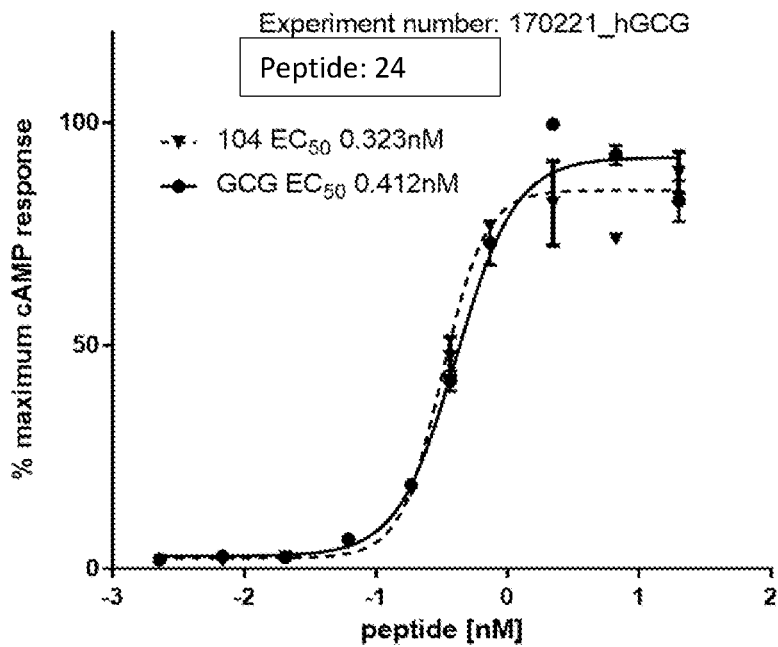
Figure 4N:
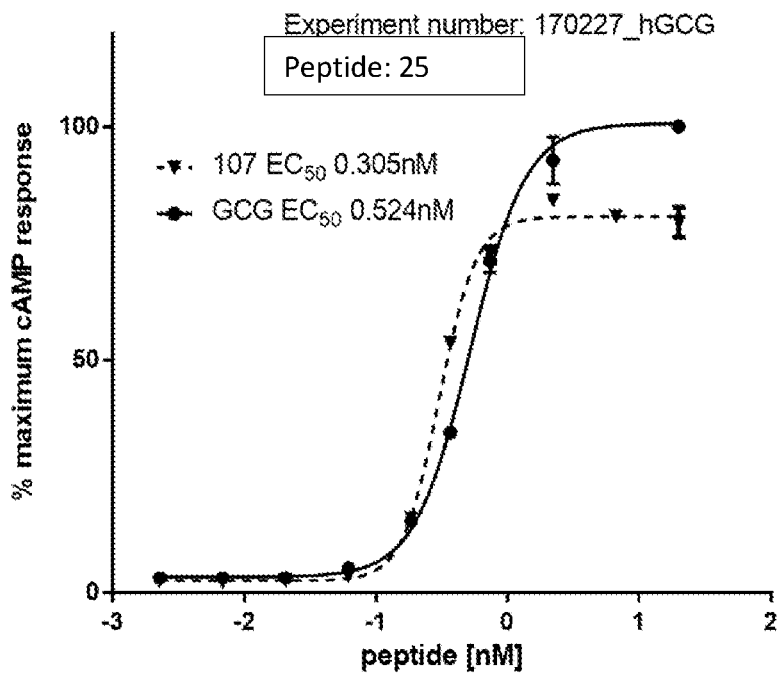
Figure 6A:
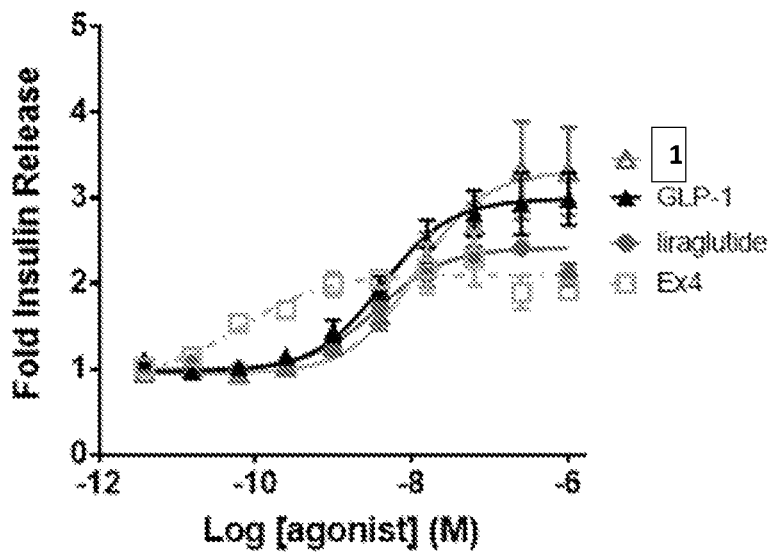
FIG. 6 shows exemplar graphs of peptide-stimulated insulin secretion, for example compounds, GLP-1, exendin-4 and liraglutide.
Figure 6B:
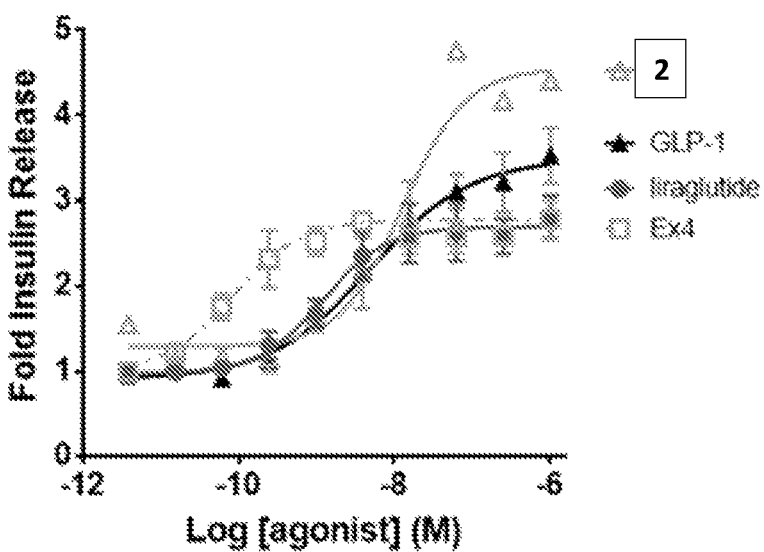
Figure 6C:
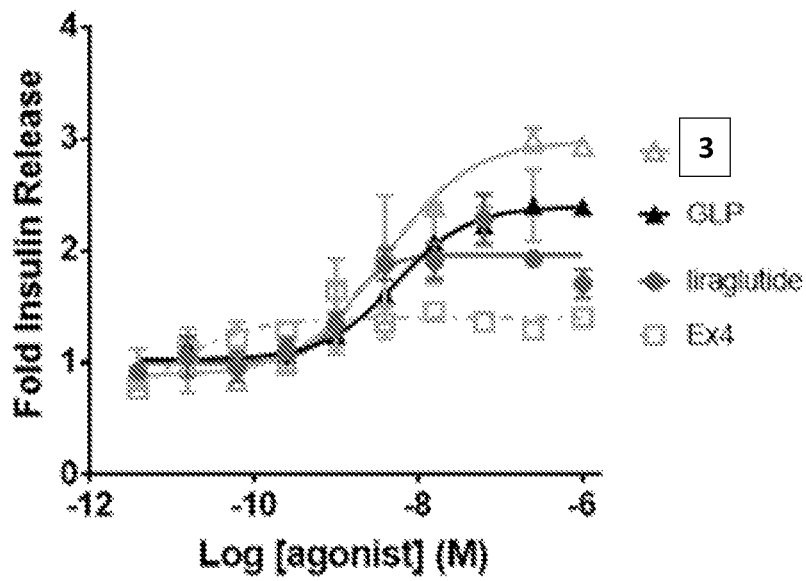
Figure 6D:
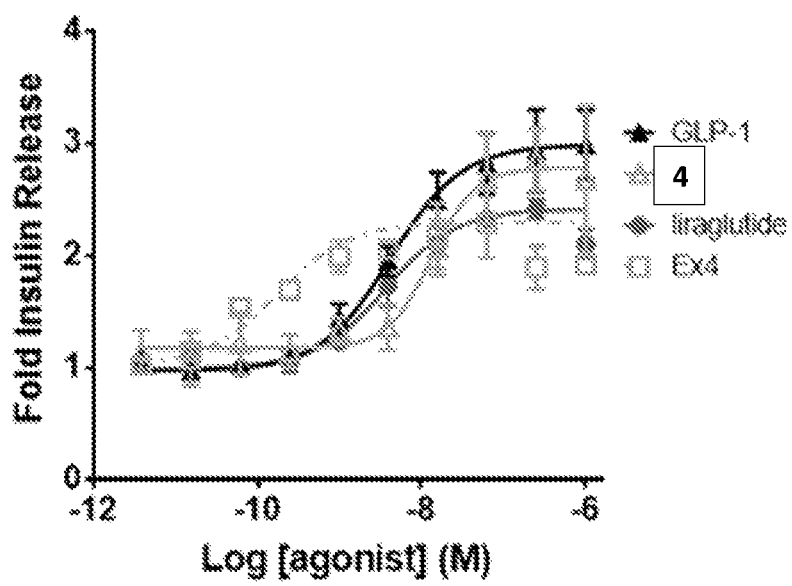
Figure 6E:
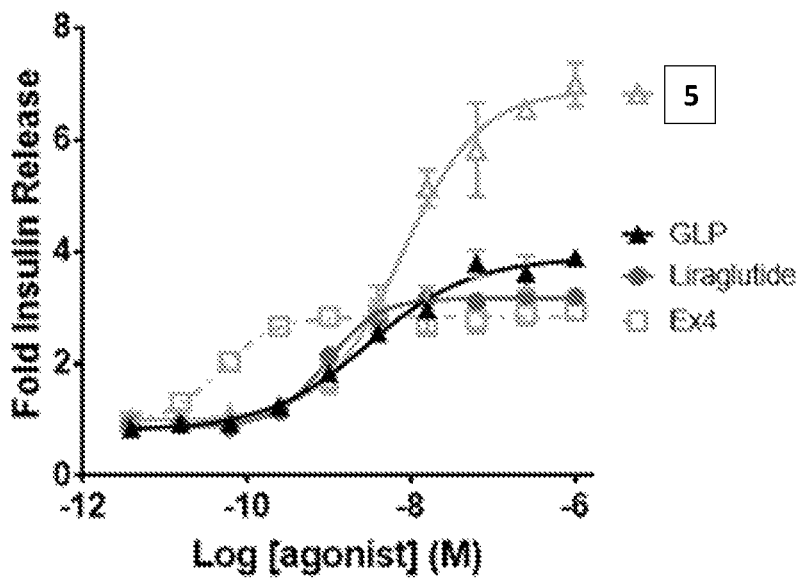
Figure 6F:
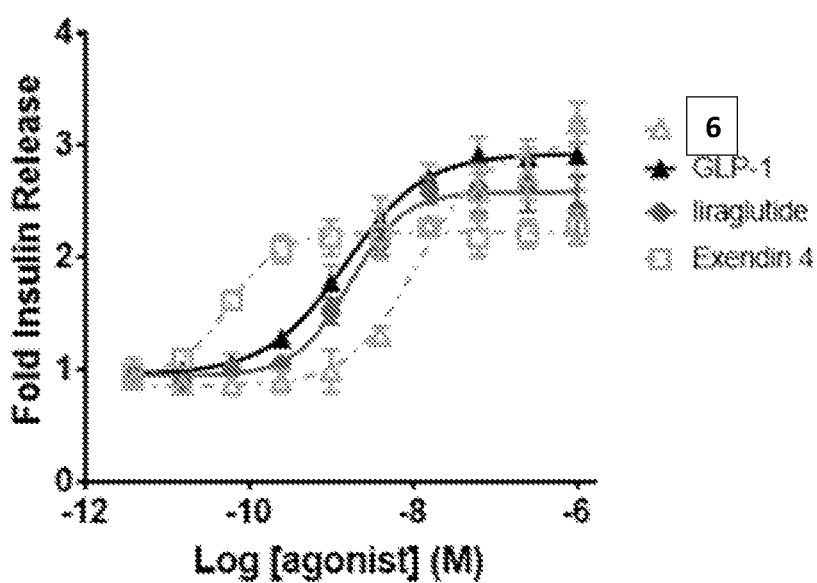
Figure 6G:
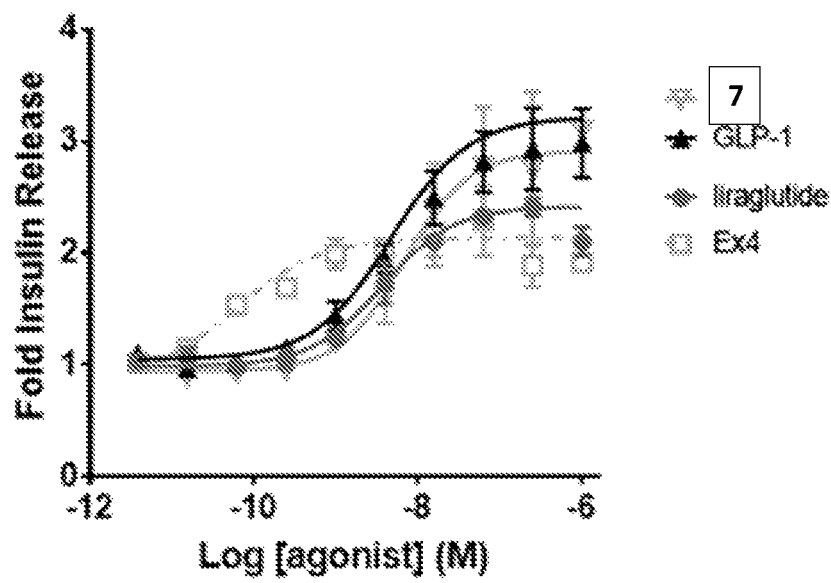
Figure 6H:
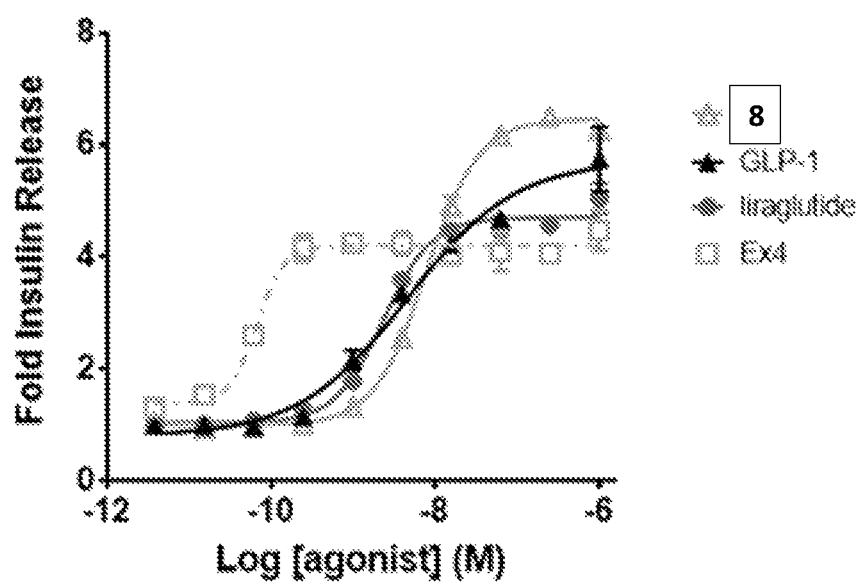
Figure 6I:
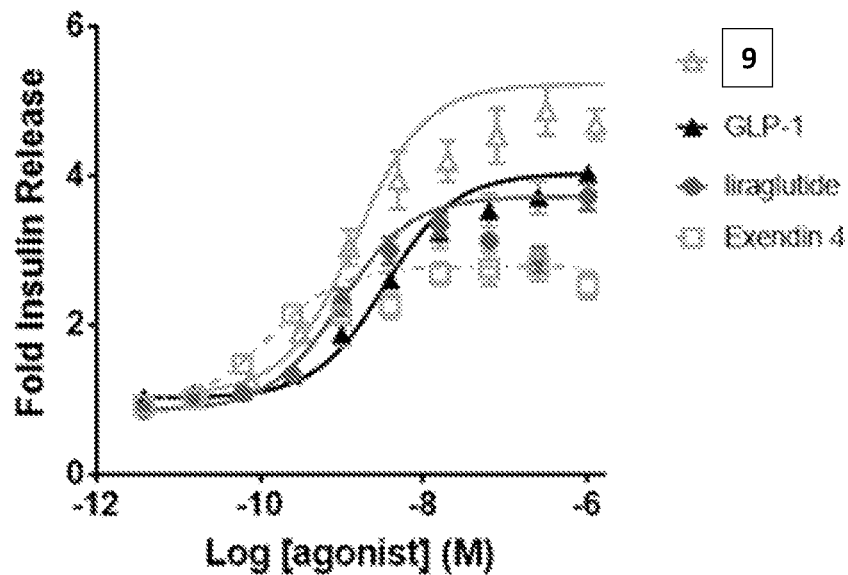
Figure 6J:
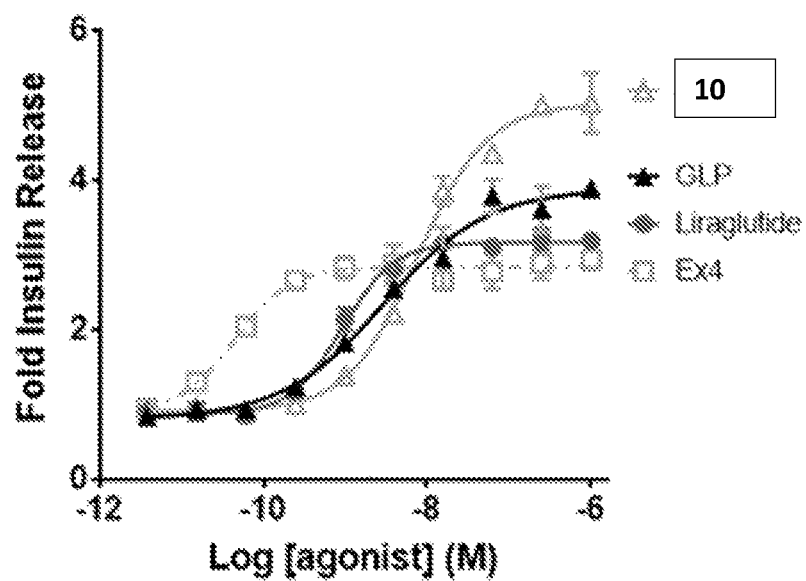
Figure 6K:
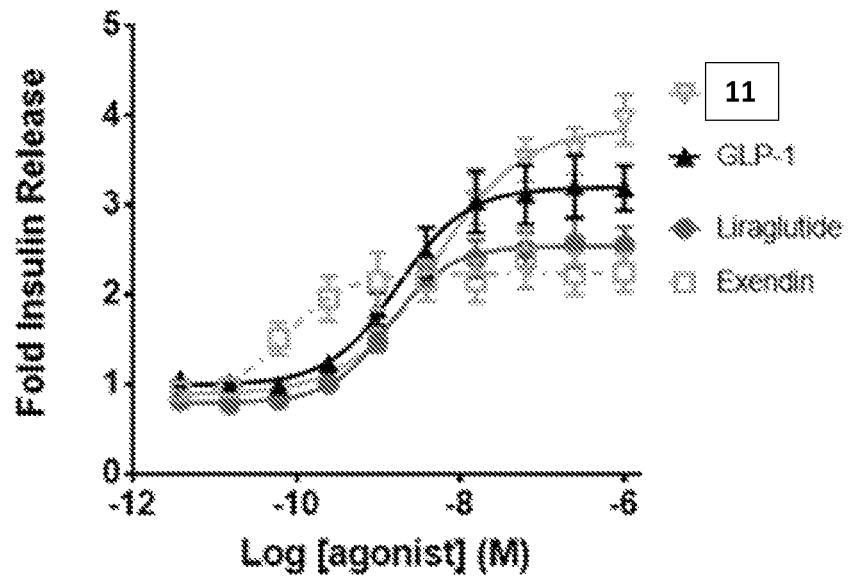
Figure 6L:
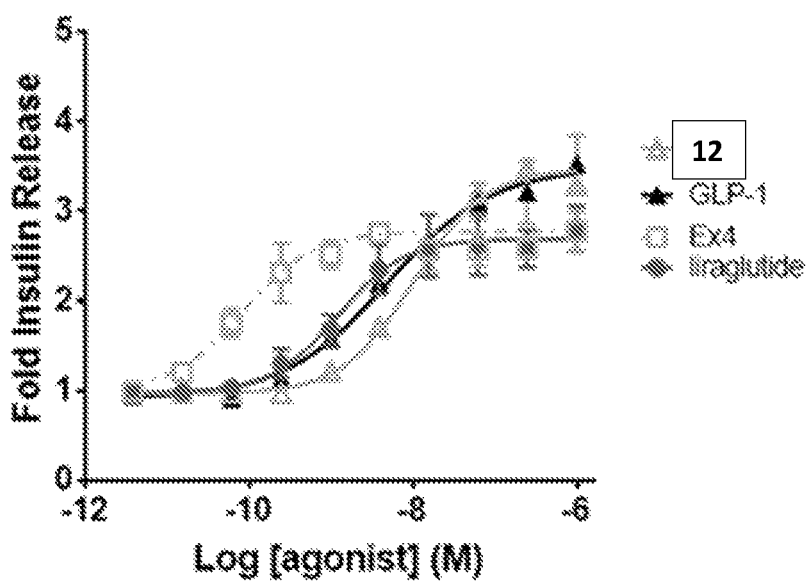
Figure 6M:
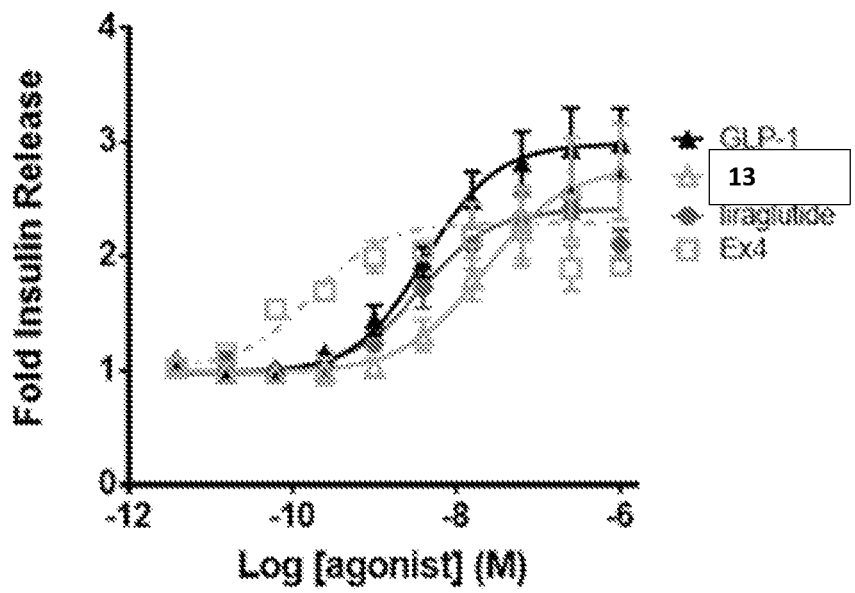
Figure 6N:
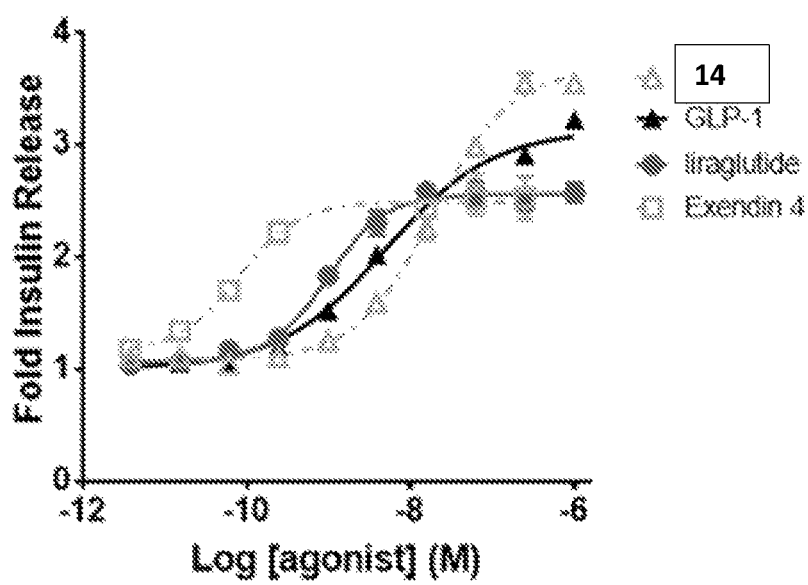
Figure 6O:
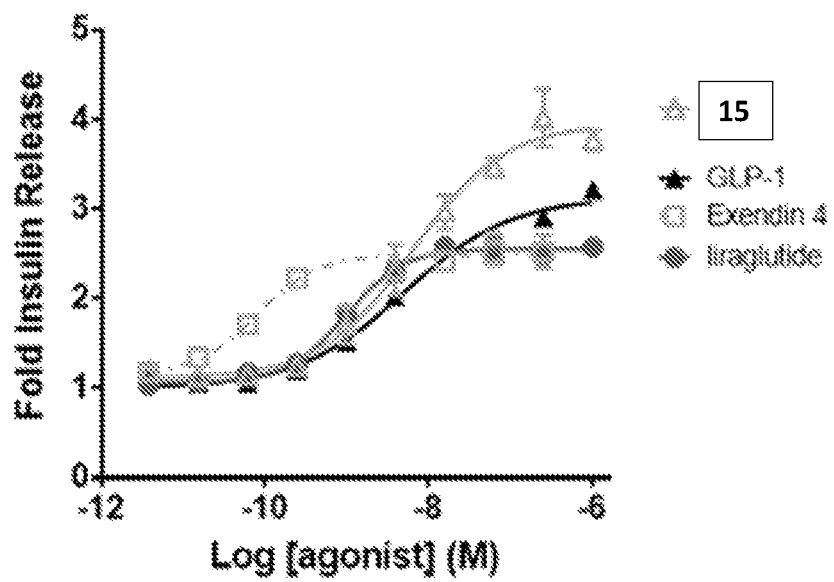
Figure 6P:
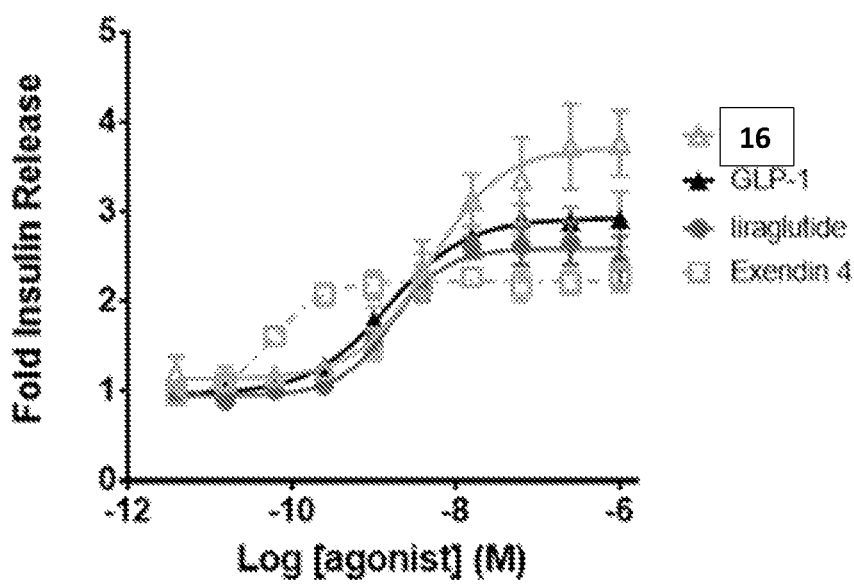
Figure 6Q:
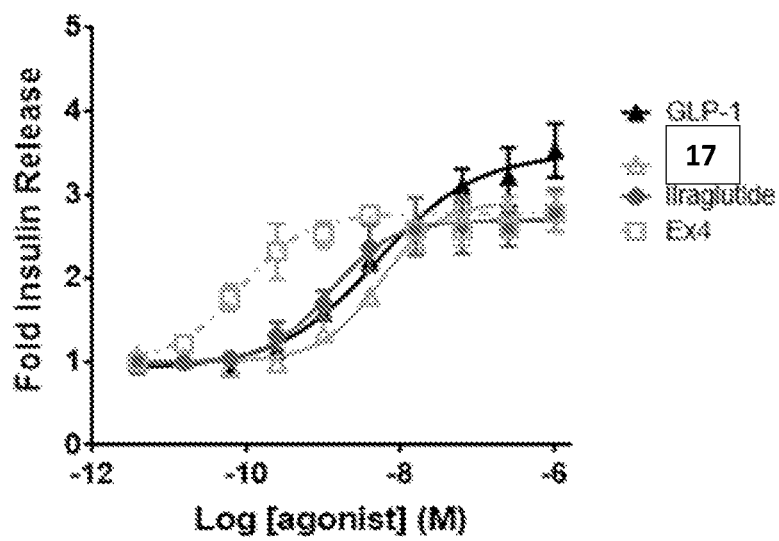
Figure 6R:
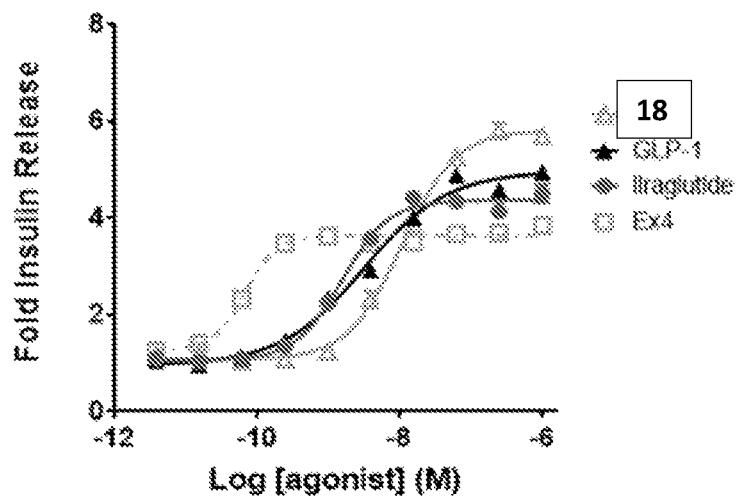
Figure 6S:
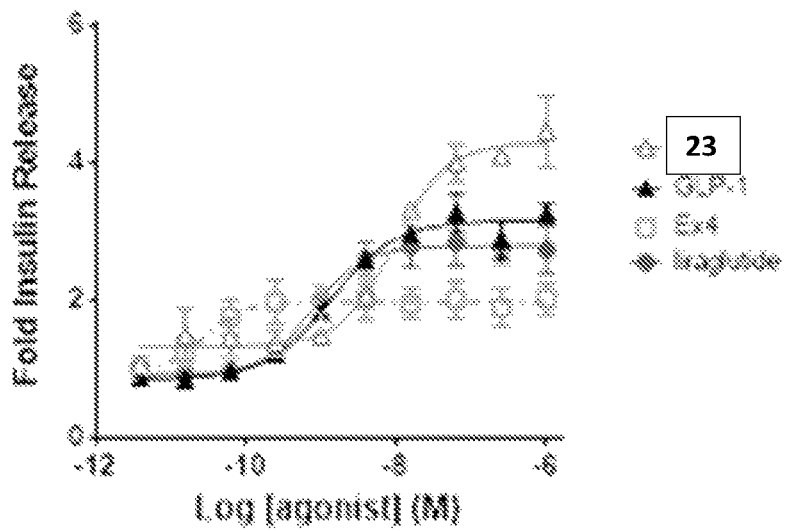
Figure 6T:
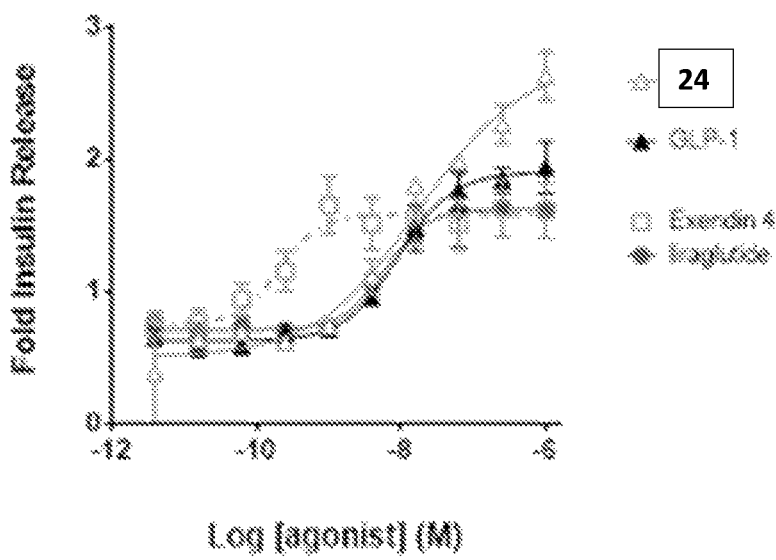
Figure 6U:
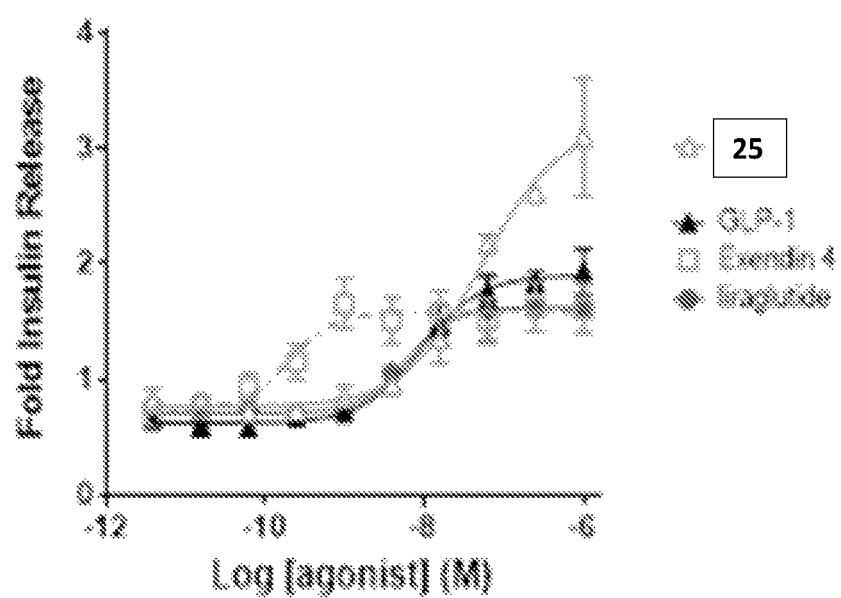

The amino acid sequences herein are shown with the N-terminus to the left, and where sequences are set out across multiple lines, the N-terminus is to the top left.

Unless indicated otherwise, the amino acid residues in the sequences are L-amino acids.

The amino acid sequences listed in the application are shown using standard letter abbreviations for amino acids. The unnatural amino acid 2-aminoisobutyric acid has its usual abbreviation 'Aib'.

The specific sequences given herein relate to specific preferred embodiments of the invention.

Definitions

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects. In preferred embodiments of the invention, the subject is a human subject.

Appetite: A natural desire, or longing for food. In one embodiment, appetite is measured by a survey to assess the desire for food. Increased appetite generally leads to increased feeding behaviour.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity (which is sometimes referred to as being "overweight" rather than obesity) corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J Clin. Nutr.* 45:1035-47, 1987). Ideal body weight will vary among species and individuals based on height, body build, bone structure, and sex.

Cardioprotection refers to the protection of cardiac cells (and especially the myocardial cells) from apoptosis, necrotic cell death or degeneration (loss of function). Cardioprotection is most often required following myocardial infarction, but may also be used in subjects suffering from ischemic heart disease (for example angina)

Cytoprotection refers to the protection of cells from apoptosis, necrotic cell death or degeneration (loss of function).

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Energy Metabolism: The body has to expend a certain amount of energy to maintain normal metabolism. In civilized man this is often set at about 2,800 Calories daily. If food consumption does not provide this, weight loss results. However, energy metabolism is also regulated, and, for example, administration of glucagon is thought to increase the metabolic rate so that a greater food intake is required to achieve energy balance and maintain weight. Thus, if food intake is maintained at the usual level, but energy metabolism is increased, weight loss will result.

Food intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual.

"Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

GLP-1: Glucagon-like peptide 1 (GLP-1) is derived from the transcription product of the proglucagon gene. The biologically active forms of GLP-1 are truncated forms known as GLP-1$_{(7-37)}$ and GLP-1$_{(7-36)}$-NH$_2$ (the designation —NH$_2$ designates an amino acid sequence in which the C-terminal amino acid has a —C(O)NH$_2$ group in place of a carboxylic acid group).

The sequence of human GLP-1$_{(7-37)}$ is His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly.

The sequence of human GLP-1$_{(7-36)}$-NH$_2$ is His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-CONH$_2$.

Glucagon: Glucagon is a peptide derived from the proglucagon gene. It is a 29-amino acid polypeptide in humans and has the sequence:

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr.

Neuroprotection refers to the protection of neurons within the nervous system (preferably within the central nervous system) from apoptosis, necrotic cell death or degeneration (loss of function). Neuroprotective treatments, including those relating to various aspects of the present invention may be required following a brain injury (for example those following physical trauma or non-traumatic injury such as stroke, brain tumours, infection, poisoning, hypoxia, ischemia, encephalopathy or substance abuse). Neuroprotective treatments, including those relating to various aspects of the present invention may also be indicated in subjects having a chronic neurodegenerative disease such as Alzheimer's disease, Parkinson's disease, Gehrig's disease or Huntington's disease.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), Obes. Res. 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 kg/m$^2$ to 29.9 kg/m$^2$ is overweight, while a BMI of 30 kg/m$^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Overweight: An individual who weighs more than their ideal body weight. An overweight individual can be obese but is not necessarily obese. For example, an overweight individual is any individual who desires to decrease their weight. In one convention, an overweight individual is an individual with a BMI of 25.0 kg/m$^2$ to 29.9 kg/m$^2$.

Oxyntomodulin (OXM): Oxyntomodulin is a 37 amino acid peptide member of the glucagon superfamily comprising the entire 29 amino acid sequence of glucagon, with an eight amino acid carboxy terminal extension, resulting from the tissue-specific processing of the pre-pro-glucagon precursor in the brain and gut. The human OXM sequence is as follows:

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala.

PEGylation and PEGylated: PEGylation refers to the process of reacting a poly(alkylene glycol), preferably an activated poly(alkylene glycol) to form a covalent bond. A facilitator may be used, for example an amino acid, e.g. lysine. Although "PEGylation" is often carried out using poly(ethylene glycol) or derivatives thereof, such as methoxy poly(ethylene glycol), the term is not limited herein to the use of methoxy poly(ethylene glycol) but also includes the use of any other useful poly(alkylene glycol), for example poly(propylene glycol). The term PEGylated refers to a compound containing such a poly(alkylene glycol) group.

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called isoelectric focusing which is an electrophoretic method that utilises a pH gradient contained within a polyacrylamide gel.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. Unless dictated otherwise by context, the terms "polypeptide", "peptide", or "protein" as used herein encompass any amino acid sequence and include modified sequences such as glycoproteins. The term "polypeptide" covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH 4 and pH 10 are usually regarded as tolerably comfortable.

Therapeutically effective amount: A dose sufficient to prevent advancement, or to cause regression of a disorder, or which is capable of relieving a sign or symptom of a disorder, or which is capable of achieving a desired result. In some embodiments, a therapeutically effective amount of a compound of the invention is an amount sufficient to inhibit or halt weight gain, or an amount sufficient to decrease appetite, or an amount sufficient to increase energy expenditure.

Compounds, Derivatives and Salts

The present invention provides compounds of formula (I), derivatives of such compounds, and salts of such compounds and derivatives.

The present inventors have found that example compounds of the invention containing Aib at position 2 and His at position 3 have properties including increasing weight loss in vivo, and/or increasing insulin secretion in beta-cells relative to administration of GLP-1, of liraglutide, or of GLP-1 and glucagon combined.

In some embodiments, Xaa12 is Arg. In other embodiments Xaa12 is Lys.

In some embodiments, Xaa16 is Ala. In other embodiments Xaa16 is Gln. In other embodiments Xaa16 is Glu. In other embodiments Xaa16 is Thr. In other embodiments Xaa16 is His. In some embodiments Xaa16 is Gln or Glu.

In some embodiments, Xaa17 is Arg. In other embodiments Xaa17 is Lys.

In some embodiments, Xaa20 is Gln. In other embodiments Xaa20 is His.

In some embodiments, Xaa21 is Glu. In other embodiments Xaa21 is Asp.

In some embodiments, Xaa28 is Thr. In other embodiments Xaa28 is His. In other embodiments Xaa28 is Ala. In other embodiments Xaa28 is Asn. In other embodiments Xaa28 is Gln. In other embodiments Xaa28 is Ser. In other embodiments Xaa28 is Ile. In other embodiments Xaa28 is Leu.

In some embodiments, Xaa29 is Gly. In other embodiments Xaa29 is Thr. In other embodiments Xaa29 is Ser. In some embodiments Xaa29 is Thr or Gly.

In an embodiment,
Xaa12 is Arg or Lys;
Xaa16 is Gln, Glu or His;
Xaa17 is Arg or Lys;
Xaa20 is Gln;
Xaa21 is Glu;
Xaa28 is Asn, His, Ala, Thr or Gln;
Xaa29 is Thr, Gly or Ser; and
V is a C-terminal sequence of formula (II):

His-His-His-His-His-Z   (II)

wherein Z is a sequence of from 1 to 6 amino acid residues, and wherein a carboxylic acid group of the amino acid residue at the C-terminus may optionally be replaced by a —C(O)NH$_2$ group.

In an embodiment,
Xaa12 is Arg or Lys;
Xaa16 is Ala, Gln, Glu or His;
Xaa17 is Arg or Lys;
Xaa20 is Gln or His;
Xaa21 is Glu;
Xaa28 is Asn, His, Ala, Thr, Leu or Gln;
Xaa29 is Thr, Gly or Ser; and
V is a C-terminal sequence of formula (II):

His-His-His-His-His-Z   (II)

wherein Z is a sequence of from 1 to 6 amino acid residues, and wherein a carboxylic acid group of the amino acid residue at the C-terminus may optionally be replaced by a —C(O)NH$_2$ group.

V is a sequence consisting of from 5 to 12 amino acid residues, wherein at least 4 of said amino acid residues are His residues, and wherein a carboxylic acid group of the amino acid residue at the C-terminus may optionally be replaced by a —C(O)NH$_2$ group.

In some embodiments, V comprises 5 amino acids. In other embodiments, V comprises 6 amino acid residues. In other embodiments, V comprises 7 amino acid residues. In other embodiments, V comprises 8 amino acid residues. In other embodiments, V comprises 9 amino acid residues. In other embodiments, V comprises 10 amino acid residues. In other embodiments, V comprises 11 amino acid residues. In other embodiments, V comprises 12 amino acid residues.

In some embodiments, the amino acid residue at the C-terminus has a C(O)NH₂ group in place of a carboxylic acid group. In some embodiments, the amino acid residue does not have a C(O)NH₂ group in place of a carboxylic acid group (i.e. the C-terminus amino acid residue terminates in a carboxylic acid/carboxylate group).

In some embodiments 4, 5 or 6 of the amino acid residues in the V group are His residues. In some embodiments, 4 of the amino residues in the V group are His residues. In some embodiments, 5 of the amino residues in the V group are His residues. In some embodiments, 6 of the amino residues in the V group are His residues.

In some embodiments, the V group has a sequence of 4, 5 or 6 His residues, followed by a sequence of from 1 to 6 amino acid residues which are not His residues. In some embodiments, the V group has a sequence of 5 His residues, followed by a sequence of from 1 to 6 amino acid residues which are not His residues. In some embodiments, the V group has a sequence of 1 Gly residue, followed by 5 His residues, followed by a sequence of 2 amino acid residues which are not His residues.

In some embodiments, the amino acid residue at the C-terminus of the peptide (i.e. the final amino acid residue in the sequence) is a Trp residue. It has unexpectedly been found that the introduction of Trp at the C-terminus can lead to increased biological activity, e.g. increased potency at the glucagon and/or GLP-1 receptor.

In some embodiments, V is a C-terminal sequence of formula (Ia):

(Gly)ₐ-His-His-His-His-His-Z    (Ia)

wherein
a is 0 or 1; and
Z is a sequence of from 1 to 6 amino acid residues, and wherein a carboxylic acid group of the amino acid residue at the C-terminus may optionally be replaced by a
s—C(O)NH₂ group.

In some embodiments, V is a C-terminal sequence of formula (Ia) in which a carboxylic acid group of the amino acid residue at the C-terminus is replaced by a —C(O)NH₂ group. In other embodiments, V is a C-terminal sequence of formula (Ia) in which a carboxylic acid group of the amino acid residue at the C-terminus is not replaced by a —C(O)NH₂ group (i.e. the C-terminus amino acid residue terminates in a carboxylic acid/carboxylate group).

In some embodiments, V is a C-terminal sequence of formula (Ia) in which a is 0. In other embodiments, V is a C-terminal sequence of formula (Ia) in which a is 1.

In some embodiments, V is a C-terminal sequence of formula (Ia) in which Z does not contain any His residues.

In some embodiments, V is a C-terminal sequence of formula (II):

His-His-His-His-His-Z    (II)

wherein Z is a sequence of from 1 to 6 amino acid residues, and wherein a carboxylic acid group of the amino acid residue at the C-terminus may optionally be replaced by a —C(O)NH₂ group.

In some embodiments, V is a C-terminal sequence of formula (II) in which a carboxylic acid group of the amino acid residue at the C-terminus is replaced by a —C(O)NH₂ group. In other embodiments, V is a C-terminal sequence of formula (II) in which a carboxylic acid group of the amino acid residue at the C-terminus is not replaced by a —C(O)NH₂ group (i.e. the C-terminus amino acid residue terminates in a carboxylic acid/carboxylate group).

In some embodiments, V is a C-terminal sequence of formula (II) in which Z does not contain any His residues.

In some embodiments, V is selected from the group consisting of:

```
His-His-His-His-His-Ser;
His-His-His-His-His-Val;
His-His-His-His-His-Ser-Val;
His-His-His-His-His-Ser-Trp;
His-His-His-His-His-Pro-Ser;
His-His-His-His-His-Pro-Thr;
His-His-His-His-His-Leu-Ser;
His-His-His-His-His-Thr-Thr;
His-His-His-His-His-Gln-Trp;
His-His-His-His-His-Pro-Ser-C(O)NH₂;
His-His-His-His-His-Gln-Gly-Trp;
His-His-His-His-His-Gly-Gln-Trp;
His-His-His-His-His-Gly-Leu-Ser;
His-His-His-His-His-Gly-Pro-Thr;
His-His-His-His-His-Pro-Ser-Trp;
His-His-His-His-His-Pro-Ser-Gly-Trp;
His-His-His-His-His-Ser-Val-Pro-Pro-Pro-C(O)NH₂;
His-His-His-His-His-Val-Ser-Pro-Pro-Pro-Trp;
and
His-His-His-His-His-Ser-Val-Pro-Pro-Pro-Trp.
```

In some preferred embodiments, the compound has an amino acid sequence of formula (III):

```
His-Aib-His-Gly-Thr-Phe-Thr-Ser-Asp-Tyr-Ser-Xaa12-
Tyr-Leu-Asp-Xaa16-Xaa17-Arg-Ala-Xaa20-Xaa21-Phe-
Ile-Glu-Trp-Leu-Leu-Xaa28-Xaa29-V  (III)
``` wherein
Xaa12 is Arg or Lys;
Xaa16 is Gln, Glu, His or Ala;
Xaa17 is Arg or Lys;
Xaa20 is Gln or His;
Xaa21 is Glu;
Xaa28 is Asn, His, Ala, Thr, Leu or Gln;
Xaa29 is Thr, Gly or Ser; and
V is a C-terminal sequence of formula:

His-His-His-His-His-Z wherein Z is a sequence of from 1 to 6 amino acid residues, and wherein a carboxylic acid group of the amino acid residue at the C-terminus may optionally be replaced by a —C(O)NH₂ group, and the derivative is a derivative of such a compound, and the salt is a salt of such a compound or derivative.

In particularly preferred embodiments, the compound consists of an amino acid sequence of formula (I), and the derivative is a derivative of such a compound, and the salt is a salt of such a compound or derivative.

In especially preferred embodiments, the compound consists of the amino acid sequence of any one of the compounds of the invention set out in the Table of FIG. 1, and the derivative is a derivative of such a compound, and the salt is a salt of such a compound or derivative.

The compounds, derivatives and salts may be produced by recombinant methods which are well-known in the art or alternatively they may be produced by synthetic methods, again which are well-known in the art.

Derivatives

Whilst in some embodiments, the invention relates to a compound of formula (I) and is not a derivative, in other embodiments the invention relates to a derivative of a compound of formula (I). The derivative may for example comprise one or more derivatisations selected from amidation, glycosylation, carbamylation, acylation, sulfation, phosphorylation, cyclization, lipidization, pegylation and fusion to another peptide or protein to form a fusion protein. The structure may be modified at random positions within the molecule, or at predetermined positions within the molecule and may include one, two, three or more attached chemical moieties.

The derivative may for example be a fusion protein, whereby the structure of formula (I) is fused to another protein or polypeptide (the fusion partner) using recombinant methods known in the art. Alternatively, such a fusion protein may be synthetically synthesized by any known method. Such a fusion protein comprises the structure of formula (I). Any suitable peptide or protein can be used as the fusion partner (e.g., serum albumin, carbonic anhydrase, glutathione-S-transferase or thioredoxin, etc.). Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers Asp-Asp-Asp-Asp-Tyr, Gly-Pro-Arg, Ala-Gly-Gly and His-Pro-Phe-His-Leu, which can be cleaved by enterokinase, thrombin, ubiquitin cleaving enzyme and renin, respectively. For details, see for example U.S. Pat. No. 6,410,707, the contents of which are incorporated herein by reference.

A derivative of the invention may for example be a physiologically functional derivative of the structure of formula (I). The term "physiologically functional derivative" is used herein to denote a chemical derivative of a compound of formula (I) having the same physiological function as the corresponding unmodified compound. For example, a physiologically functionally derivative may be convertible in the body to a compound of formula (I). According to the present invention, examples of physiologically functional derivatives include esters, amides, and carbamates; preferably esters and amides.

Pharmaceutically acceptable esters and amides of the compounds of the invention may comprise a $C_{1-20}$ alkyl-, $C_{2-20}$ alkenyl-, $C_{5-10}$ aryl-, $C_{5-10}$ ar-$C_{1-20}$ alkyl-, or amino acid- ester group or amide group attached at an appropriate site, for example formed by reaction of an alkyl, alkenyl aryl, aralkyl or amino alkyl group containing an alcohol or amino moiety with an acid moiety present in the compound of formula (I), or formed by reaction of an alkyl, alkenyl aryl, aralkyl or amino alkyl group containing an activated acyl group with an alcohol or amine group present in the compound of formula (I). Examples of suitable moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H29$) or stearyl ($C_7H_{35}$)) and bile acids (e.g. cholate or deoxycholate).

Methods for lipidization of sulfhydryl-containing compounds with fatty acid derivatives are disclosed in U.S. Pat. Nos. 5,936,092; 6,093,692; and 6,225,445, the contents of which are incorporated herein by reference. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in a lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H_{29}$) or stearyl ($C_{17}H_{35}$)) and bile acids (e.g. cholate or deoxycholate).

Cyclization methods include cyclization through the formation of a disulfide bridge, and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

The derivative may for example be a PEGylated structure of formula (I). Derivatives which are PEGylated compounds of the invention may provide additional advantages such as increased solubility, stability and circulating time of the polypeptide, or decreased immunogenicity (see U.S. Pat. No. 4,179,337, the contents of which are incorporated herein by reference).

Chemical moieties for derivatisation of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any, on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

Salts

Salt forms of compounds of formula (I) and of derivatives of such compounds also form part of the invention. In some embodiments the salt is a salt of a compound of formula (I). In other embodiments the salt is a salt of a derivative of a compound of formula (I).

Salts of compounds of the invention include those which are pharmaceutically acceptable, i.e. which are suitable for use in medicine. However, salts having non-pharmaceutically acceptable counterions are also within the scope of the present invention, for example, for use as intermediates in the preparation of the analogues.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycolic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic acid may be useful as intermediates in obtaining the analogues of the invention in final form.

Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Solvates

Those skilled in the art of organic and/or medicinal chemistry will appreciate that many organic compounds can form complexes with solvents in which they are reacted or from which they are precipitated or crystallized. Such complexes are known as "solvates". For example, a complex with water is known as a "hydrate". The invention also encompasses solvates of the compounds of formula (I), solvates of derivatives of the compounds, and solvates of salts of the derivatives.

Those skilled in the art of organic and/or medicinal chemistry will also appreciate than many organic compounds can exist in different forms, including as amorphous material and/or in one or more crystalline forms. Different physical forms of organic compounds are known as polymorphs. The invention also encompasses all such different physical forms of the compounds of formula (I), as well as different physical forms of their derivatives and salts.

Biological Activity

Compounds of the invention have agonistic activity at the human glucagon receptor and thus can be considered to be glucagon receptor agonists. This may be assessed by, for example, an in vitro or cellular binding assay or by a reporter assay. Preferred compounds of the invention exhibit an activity at the human glucagon receptor which is at least $1/10^{th}$ that of human glucagon, preferably an activity which is at least $1/5^{th}$, $1/3^{rd}$ or $1/2$ that of human glucagon, for example when tested in accordance with the assay described in the examples section below. More preferred compounds of the invention exhibit an activity at the human glucagon receptor which is at least equivalent to that of human glucagon.

Methods of assessing activity at the glucagon receptor are well known. For example, Thermo Scientific (Lafayette, Colo., USA) market an in vitro glucagon receptor assay.

Compounds of the invention also have activity at the human GLP-1 receptor and can be considered GLP-1 receptor agonists. This may be assessed by, for example, an in vitro or cellular binding assay or by a reporter assay. Preferred GLP-1 analogues of the invention exhibit an activity at the human GLP-1 receptor that is at least $1/20^{th}$ that of human GLP-1, preferably an activity which is at least $1/10^{th}$, $1/5^{th}$, $1/3^{rd}$ or $1/2$ that of human GLP-1, for example when tested in accordance with the assay described in the examples section below. More preferred compounds of the invention exhibit an activity at the human GLP-1 receptor that is at least equivalent to that of human GLP-1.

Methods of assessing activity at the GLP-1 receptor are well known. For example, Mukai et al (2009) Biochem. Biophys. Re. Comm. 28993:523-6 discloses a method of assaying for GLP-1 receptor binding. A specific method is described herein below.

Preferred compounds of the invention have greater activity in promoting insulin release/secretion than at least one of GLP-1, the combination of GLP-1 and glucagon, and liraglutide (e.g. at equivalent concentration or dose). This may be assessed by, for example, an in vitro assay. Methods of assessing release of insulin from beta-cells are well known. A specific method is described herein below.

Compounds of the invention fulfil some, or more preferably all, of the following criteria:

1) Sustained bioactivity at the human glucagon receptor resulting in enhancement of energy expenditure;
2) Sustained bioactivity at the human GLP-1 receptor resulting in inhibition of appetite.
3) Improved activity in promoting insulin release from beta-cells relative to GLP-1, and/or relative to the combination of GLP-1 and glucagon, and/or relative to liraglutide;
4) Low incidence of side effects such as nausea and vomiting, particularly at therapeutically effective dosage levels;
5) High solubility in aqueous solution at pH 5 to allow an effective dose to be administered in a low volume injection (thereby resulting in lower pain of injection). Solubility may be easily assessed by simple in vitro tests;
6) Long period of activity in vivo (as assessed in humans or an animal model) so as to permit injections no more frequently than daily and preferably no more than twice, or more preferably no more than once a week, whilst still producing acceptable therapeutic or cosmetic benefits;
7) Good weight loss or appetite suppression (as assessed in human subjects or an animal model);
8) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm ((Jameson & Wolf (1988) Comput. Appl. Biosci. 4(1):181-6), or the PREDI-TOP algorithm (Pellequer & Westhof, (1993) J. Mol. Graph. 11(3):204-10, or using the methods of Kolaskar &

Tongankar (1990) FEBS Leu. 10:276(1-2):172-4, the contents of which are incorporated herein by reference);

According to certain embodiments of the invention, especially embodiments relating to weight loss, obesity, carbohydrate metabolism and diabetes, the compounds, derivatives and salts of the invention have one, several or all of the following features:

A) Sufficient solubility between pH 4 and pH 5 to permit an effective dose to be administered in a volume of less than 1 ml, less than 0.5 ml or less than 0.3 ml;
B) Activation of cAMP signalling in human embryonic kidney cells over-expressing the human GLP-1 Receptor;
C) Activation of cAMP signalling in cells over-expressing the human glucagon receptor;
D) One, several or all of the further 1 to 8 features listed above.

Pharmacokinetics, Duration of Action and Solubility

Compounds of the present invention exhibit potent and prolonged duration of action in vivo following subcutaneous administration. In order to achieve this, the compounds are required to have both good activity at the biological target, and excellent pharmacokinetic properties.

Incorporation of His residue(s) into peptides having poor aqueous solubility typically leads to peptides having enhanced solubility at acidic pH (e.g. pH 5) due to the presence of charged His side-chain groups, but which are less soluble at physiological pH (pH 7.4). The pI of the side-chain group of histidine is about 6.0. Such properties enable formulation of His-containing peptides in weakly acidic media. Upon subcutaneous injection of such formulations, the solubility falls leading to subcutaneous precipitation of peptide which resolubilises over time. Zinc-containing formulations of His-containing peptides enhance this effect, because at pH 7.4 but not at pH 5 zinc ions co-ordinate with histidine residues and result in a further reduction in solubility which can contribute to increased precipitation at a subcutaneous injection site, or which can contribute to increased stability of the precipitate. However, where precipitation of peptide is not sufficiently rapid following subcutaneous administration, there may still be an initial "spike" or "burst" in blood concentration levels of the peptide. Such properties are undesirable since they increase the possibility of subjects experiencing side effects associated with high concentration levels of the peptides, such as nausea, even if only temporary. In contrast to peptides not having the multi-His containing C-terminal sequence of the invention, the present compounds either do not display initial "spikes" or "bursts" in plasma concentration levels following subcutaneous administration or any such "burst" is significantly reduced. This reduces the likelihood and/or severity of possible side effects associated with high circulating levels of the compounds.

Conditions

The invention also provides a compound, derivative or salt of the invention, or a composition comprising the compound, derivative or salt together with a pharmaceutically acceptable carrier and optionally a further therapeutic agent, for use as a medicament.

The invention also provides a method of treating or preventing a disease or disorder or other non-desired physiological state in a subject comprising administration of a therapeutically effective amount of a compound, derivative or salt of the invention, or of a composition comprising the compound, derivative or salt together with a pharmaceutically acceptable carrier and optionally a further therapeutic agent.

Preferably the compound, derivative, salt or composition is administered subcutaneously.

According to certain embodiments, the disease or disorder or other non-desired physiological state is diabetes or obesity, and particularly diabetes (e.g. type II diabetes).

According to certain embodiments, the disease or disorder or other non-desired physiological state may be the physiological state of being overweight.

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes.

In addition, or alternatively, the subject may have, or may be at risk of having, a disorder in which obesity or being overweight is a risk factor. Such disorders include, but are not limited to, heart disease, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acanthosis nigricans; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, *Nature* 404: 635-43; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia (see e. g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatal hernia.

In some embodiments, the disease or disorder may be non-alcoholic fatty liver disease.

According to certain embodiments the disease or disorder or other non-desired physiological state may be being of a non-desired weight despite not being obese or overweight. The subject may be of normal weight (this includes but is not limited to subjects who were previously overweight or obese and who wish to prevent a return to an unhealthy weight). A subject may be a subject who desires weight loss, for example female and/or male subjects who desire a change in their appearance. In some cases where the subject is of a normal weight, aspects of the invention may relate to cosmetic treatment rather than to therapeutic treatment.

The invention also provides a method of increasing the energy expenditure of a subject, reducing appetite in a subject (e.g. due to bioactivity at the GLP-1 receptor, rather than being associated with nausea or vomiting), reducing food intake in a subject, reducing calorie intake in a subject, improving insulin release in a subject, improving carbohydrate metabolism in a subject, and/or improving carbohydrate tolerance in a subject, comprising administration of a therapeutically effective amount of a compound, derivative, salt or composition of the invention. Such methods may relate to treating subjects having a pre-diabetic state such as insulin insensitivity or pre-diabetes.

Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect, the method of the invention involves manipulation of the arcuate circuitry that alter food intake coordinately and reciprocally alter energy expenditure. Energy expenditure is a result of cellular metabolism, protein synthesis, metabolic rate, and calorie utilization. Thus, in this aspect of the invention, administration of a compound, derivative, salt or composition of the invention results in increased energy expenditure, and decreased efficiency of calorie utilization.

The increase in energy expenditure may manifest as a lessening of the normal reduction in energy expenditure seen following reduced food intake, or it may manifest as an absolute increase in energy expenditure for example by the promotion of increased physical activity levels or by an increase in the basal metabolic rate.

The invention also provides a method for improving a lipid profile in a subject comprising administration of a therapeutically effective amount of a compound, derivative, salt or composition of the invention. The invention also provides a method for alleviating a condition or disorder that can be alleviated by reducing nutrient availability comprising administration of a therapeutically effective amount of a compound, derivative, salt or composition of the invention.

A compound, derivative, salt or composition of the invention may be used for weight control and treatment, for example reduction or prevention of obesity, in particular any one or more of the following: preventing and reducing weight gain; inducing and promoting weight loss; and reducing obesity as measured by the Body Mass Index. A compound, derivative, salt or composition of the invention may be used in maintaining any one or more of a desired body weight, a desired Body Mass Index, a desired appearance and good health.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

J. Cereb. Blood Flow Metab. 2011 Apr. 13 (Teramoto S et al) discusses the use of both GLP-1 and exendin-4 to confer cardioprotection after myocardial infarction and demonstrates that exendin-4 may be used to provide neuroprotection against cerebral ischemia-reperfusion injury. The study showed that mice receiving a transvenous injection of exendin-4, after a 60-minute focal cerebral ischemia showed significantly reduced infarct volume and improved functional deficit as well as suppressed oxidative stress, inflammatory response, and cell death after reperfusion. The study provided evidence that the protective effect of exendin-4 is mediated through increased intracellular cAMP levels and suggested that exendin-4 is potentially useful in the treatment of acute ischemic stroke.

Accordingly, the invention also provides a method of providing cytoprotection in a subject, such as providing cardiac protection, providing neuroprotection and/or treating or preventing neurodegeneration, comprising administration of a therapeutically effective amount of a compound, derivative, salt or composition of the invention.

In certain embodiments the disease or disorder or other non-desired physiological state which the compound, derivative, salt or composition of the invention may be used to treat or prevent is neurodegeneration. Such neurodegeneration may be caused by apoptosis, necrosis or loss of function of neuronal cells, preferably in the CNS. Neurodegeneration treated or prevented may be that following a brain injury (for example following physical trauma or following a non-traumatic injury such a stroke, tumor, hypoxia, poisoning, infection, ischemia, encephalopathy or substance abuse). Alternatively or additionally, neurodegeneration may be prevented or treated in a subject having (or diagnosed as having a predisposition to) a neurodegenerative disease such as Alzheimer's disease, Parkinson's disease, Gehrig's disease (Amyotrophic Lateral Sclerosis), Huntington's disease, Multiple Sclerosis, other demyelination related disorders, senile dementia, subcortical dementia, arteriosclerotic dementia, AIDS-associated dementia, other dementias, cerebral vasculitis, epilepsy, Tourette's syndrome, Guillain Barre Syndrome, Wilson's disease, Pick's disease, neuroinflammatory disorders, encephalitis, encephalomyelitis, meningitis, other central nervous system infections, prion diseases, cerebellar ataxias, cerebellar degeneration, spinocerebellar degeneration syndromes, Friedrich's ataxia, ataxia teangiectasia, spinal dysmyotrophy, progressive supranuclear palsy, dystonia, muscle spasticity, tremor, retinitis pigmentosa, striatonigral degeneration, mitochondrial encephalomyopathies, neuronal ceroid lipofuscinosis. Preferably, the neurodegenerative disease is selected from the group consisting of Alzheimer's disease, Parkinson's disease, Gehrig's disease (Amyotrophic Lateral Sclerosis) and Huntington's disease. In such circumstances the treatment would be regarded as neuroprotective. According to certain preferred embodiments, the treatment is neuroprotective following cerebral ischemia or neuroprotective in a subject having a neurodegenerative disease or diagnosed as having a predisposition to a neurodegenerative disease.

According to other embodiments the disease or disorder or other non-desired physiological state is cardiac degeneration (in particular myocardial degeneration by apoptosis, necrosis or loss of function of myocardial cells), in which case the compound, derivative, salt or composition according to the invention provides cardiac protection. According to certain preferred embodiments that treatment is protective of myocardial function following myocardiac infarction.

The invention also provides a compound, derivative, salt or composition of the invention, for use in the treatment of obesity or diabetes.

The invention also provides a compound, derivative, salt or composition of the invention, for use in increasing energy expenditure of a subject, improving insulin release in a subject, improving carbohydrate tolerance in a subject and/or improving carbohydrate metabolism in a subject. Such use may relate to treating subjects having a pre-diabetic state such as insulin insensitivity or pre-diabetes.

The invention also provides a compound, derivative, salt or composition of the invention, for use in the reduction of appetite in a subject, use in the reduction of food intake in a subject, use in the reduction of calorie intake in a subject, use in improving insulin release in a subject, and/or use in improving carbohydrate tolerance in a subject. Such use may relate to treating subjects having a pre-diabetic state such as insulin insensitivity or pre-diabetes.

The invention also provides a compound, derivative, salt or composition of the invention, for use as a cytoprotective agent (e.g. in treating or preventing neurodegeneration, providing neuroprotection and/or providing cardiac protection). For example, the compound, derivative, salt or composition may be for use in myocardial protection in a subject following myocardial infarction, or for use in neuroprotection in a subject following cerebral ischemia or stroke, or for use in neuroprotection in a subject having a chronic neurodegenerative disease. Various features of neuroprotective or cardioprotective use of the compound, derivative, salt or composition may be as outlined above in relation to methods of the invention.

In the case of neuroprotection, the subject may have experienced previously a brain injury, stroke or other event causing cerebral ischemia. Alternatively, the subject may have or have been diagnosed with a predisposition to develop a chronic neurodegenerative disease. In the case of cardioprotection the subject may have experienced previously an event causing myocardial ischemia such as a myocardial infarction and angina. According to some embodiments a compound, derivative, salt or composition of the invention may be administered as soon as possible after the subject has experienced a suspected myocardial infarction. According to certain embodiments a compound, derivative, salt or composition of the invention may be administered as soon as possible after the subject has experienced as suspected stroke.

The invention also provides use of a compound, derivative, salt or composition of the invention for the manufacture of a medicament for the treatment of obesity or diabetes, of a subject, who may be as described above in reference to other aspects of the invention.

The invention also provides use of a compound, derivative or salt of the invention for the manufacture of a medicament for increasing energy expenditure in a subject, for improving insulin release in a subject, for improving carbohydrate tolerance in a subject and/or improving carbohydrate metabolism in a subject. Such use may relate to treating subjects with a pre-diabetic state such as insulin insensitivity or pre-diabetes.

The invention also provides use of a compound, derivative or salt of the invention for the manufacture of a medicament for the reduction of appetite in a subject, reducing food intake in a subject, reducing calorie intake in a subject, improving insulin release in a subject, and/or use in improving carbohydrate tolerance in a subject.

The invention also provides use of a compound, derivative or salt of the invention for the manufacture of a medicament for providing cytoprotection (e.g. preventing or treating neurodegeneration, providing neuroprotection and/or providing cardiac protection) of a subject, who may be as described above in reference to other aspects of the invention.

According to certain embodiments the compound, derivative, salt or composition of the invention is to be administered parentally. According to other embodiments the compound, derivative, salt or composition of the invention is administered subcutaneously, intravenously, intramuscularly, intranasally, transdermally or sublingually. According to other embodiments the compound, derivative, salt or composition of the invention is administered orally. In one preferred embodiment compound, derivative, salt or composition of the invention is administered subcutaneously.

The compound, derivative, salt or composition of the invention is preferably used in the treatment of a human subject. However, while the compound, derivative, salt or composition of the invention will typically be used to treat human subjects they may also be used to treat similar or identical conditions in other vertebrates for example other primates; farm animals for example swine, cattle and poultry; sport animals for example horses; or companion animals for example dogs and cats.

Compositions

It is preferable for the compound of formula (I), or the derivative and/or the salt thereof, to be present in a pharmaceutical formulation or composition. Accordingly, the invention provides a composition comprising a compound, derivative or salt of the invention together with a pharmaceutically acceptable excipient and optionally another therapeutic ingredient. Compositions comprising the compound, derivative or salt are suitable for pharmaceutical use. According to certain preferred embodiments the composition is present in a syringe or other administration device for subcutaneous administration to humans. According to certain preferred embodiments the composition has a pH of less than 5 and/or the composition comprises zinc ions. Compositions of the invention may take the form of a pharmaceutical formulation as described below.

The pharmaceutical formulations according to the invention include those suitable for oral, parenteral (including subcutaneous, intradermal, intramuscular, intravenous, and intra-articular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988, the contents of which are incorporated herein by reference.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds or, particularly in the case of extended release, by the use of devices such as subcutaneous implants or osmotic pumps. The present compounds may also be administered liposomally.

Preferably, compositions according to the invention are suitable for subcutaneous administration, for example by injection. According to certain embodiments the composition may contain metal ions, for example copper, iron, aluminium, zinc, nickel or cobalt ions. The presence of such ions may limit solubility and thus delay absorption into the circulatory system from the site of subcutaneous administration. In a particularly preferred embodiment, the composition contains zinc ions (preferably at a molar ratio of 1:4, 1:2, 1:1, 2:1 or 4:1 of zinc ions to compound, derivative or salt of the invention, or at a ratio which is a range between any two of the whole number ratios given immediately above, e.g. at a molar ratio in the range of from 1:4 to 4:1).

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of the invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use.

Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include any compounds known to be deleterious to peptide compounds.

Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds, derivatives and salts of the invention may also be suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically, for example as a powder, ointment, gel, drop or transdermal patch; bucally; or as an oral or nasal spray.

Preparations for administration can be suitably formulated to give controlled release of compounds, derivatives and salts of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of particles of the compounds of the invention. These compositions exhibit certain biocompatibility features which allow a controlled release of the active substance, see U.S. Pat. No. 5,700,486, the contents of which are incorporated by reference.

Controlled release of compounds, derivatives and salts of the invention may also be achieved by the use of pharmaceutical compositions comprising zinc ions. As described above, at pH 7.4 but not at pH 5 zinc ions co-ordinate with histidine residues and result in increased precipitation at a subcutaneous injection site. A zinc-containing precipitate will more gradually re-dissolve because the solubilisation is dependent on the zinc washing out of the injection site into the circulation and/or surrounding tissue fluid, increasing the longevity of the release into the circulation. The use of a controlled release composition is preferred for indications such as the treatment of obesity and/or diabetes, where maximising the time period between injections is desirable. However, for indications such as providing neuroprotection or cardiac protection (e.g. following suspected myocardial infarction or stroke), where it is desired to achieve a therapeutic plasma concentration of the active agent in as short a time period as possible, an immediate release formulation will be preferred. In such cases, a dosage regime comprising administration of a dose of an immediate release formulation of the active agent (i.e. as soon as possible after suspected myocardial infarction or stroke) and subsequent administration of a dose of a controlled release formulation of the active agent may be preferred.

A compound, derivative or salt of the invention may be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by a continuous subcutaneous infusion, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990) which is incorporated herein by reference. In another aspect of the disclosure, GLP-1 analogues of the invention are delivered by way of an implanted pump, described, for example, in U.S. Pat. Nos. 6,436,091; 5,939,380; 5,993,414, the contents of which are incorporated herein by reference.

Implantable drug infusion devices are used to provide patients with a constant and long-term dosage or infusion of a drug or any other therapeutic agent. Essentially such device may be categorized as either active or passive. A compound, derivative or salt of the present invention may be formulated as a depot preparation. Such a long acting depot formulation can be administered by implantation, for example subcutaneously or intramuscularly; or by intramuscular injection. Thus, for example, the active ingredient can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of the active agent of the invention may be administered as a single pulse dose, as a bolus dose, or as pulse doses administered over time. Thus, in pulse doses, a bolus administration of the active agent is provided, followed by a time period wherein no active agent is administered to the subject, followed by a second bolus administration. In specific, non-limiting examples, pulse doses are administered during the course of a day, during the course of a week, or during the course of a month.

In certain embodiments, a therapeutically effective amount of a compound, derivative, salt or composition of the invention is administered with a therapeutically effective amount of a further agent. The compound, derivative or salt may for example be administered simultaneously with the further therapeutic agent, or it may be administered sequentially or separately. Accordingly, the invention provides a compound, derivative or salt of the invention for use as a medicament, wherein the compound, derivative or salt is for use with a therapeutically effective amount of a further therapeutic agent (e.g. for administration simultaneously, sequentially or separately). In certain embodiments, the active agent of the invention is formulated and administered with a further therapeutic agent as a single dose.

In certain embodiments, the further therapeutic agent is an additional anti-diabetic, appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, phendimetrazine, benzphetamine, sibutramine, rimonabant, topiramate, fluoxetine, bupropion, zonisamide, naltrexone, orlistat and cetilistat. Specific, non-limiting examples of an additional anti-diabetic agent include metformin, phenformin, rosiglitazone, pioglitazone, troglitazone, repaglinide, nateglinide, tolbutamide, acetohexamide, tolazamide, chlorpropamide, glipizide, glyburide, glimepiride, gliclazide, fibroblast growth factor 21, miglitol, acarbose, exenatide, pram lintide, vildagliptin and sitagliptin.

In alternative embodiments, the further therapeutic agent is an additional cardioprotective or neuroprotective agent. Specific, non-limiting, examples of additional cardioprotective agents include aspirin, N-acetylcysteine, phenethylamines, coenzyme Q10, vitamin E, vitamin C, L-carnitine, carvedilol and dexrazoxane. Specific, non-limiting examples of neuroprotective agents include statins such as simvastatin, steroids such as progesterone, minocycline, resveratrol and vitamin E. Examples of agents used for the treatment of Parkinson's disease include anticholinergics, pramipexole, bromocriptine, levodopa, carbidopa, rasagiline, amantadine and ropinirole.

A compound, derivative, salt or composition of the invention may be administered whenever the effect, e.g., appetite suppression, decreased food intake, increased energy expenditure or decreased caloric intake, is desired, or slightly before to whenever the effect is desired, such as, but not limited to, about 10 minutes, about 15 minutes, about 30 minutes, about 60 minutes, about 90 minutes, or about 120 minutes, before the time the effect is desired.

The therapeutically effective amount of the active agent of the invention will be dependent on the molecule utilized, the subject being treated, the severity and type of the affliction, and the manner and route of administration. For example, a therapeutically effective amount of a compound of the invention may vary from about 0.01 µg per kilogram (kg) body weight to about 1 g per kg body weight, for example about 0.1 µg to about 20 mg per kg body weight, for example about 1 µg to about 5 mg per kg body weight, or about 5 µg to about 1 mg per kg body weight.

In one embodiment of the invention, a compound, derivative or salt of the invention may be administered to a subject at from 4 to 1,333 nmol per kg bodyweight, for example from 5 to 1,000 nmol per kg bodyweight, for example at from 10 to 750 nmol per kg bodyweight, for example at from 20 to 500 nmol per kg bodyweight, in particular at from 30 to 240 nmol per kg bodyweight. For a 75 kg subject, such doses correspond to dosages of from 300 nmol to 100 µmol, for example from 375 nmol to 75 µmol, for example from 750 nmol to 56.25 µmol, for example from 1.5 to 37.5 µmol, in particular from 2.25 to 18 µmol. The invention also contemplates dosages ranges bounded by any of the specific dosages mentioned herein.

In an alternative embodiment, a compound, derivative or salt of the invention may be administered to a subject at 0.5 to 135 picomole (pmol) per kg body weight, for example 5 to 100 pmol per kg body weight, for example 10 to 90 pmol per kg body weight, for example about 72 pmol per kg body weight. In one specific, non-limiting example, a compound of the invention is administered in a dose of about 1 nmol or more, 2 nmol or more, or 5 nmol or more. In this example, the dose of the compound of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, examples of non-limiting dose ranges of compounds, derivatives and salts of the invention are within the range of from 1 to 100 nmols, from 2 to 90 mols, from 5 to 80 nmols.

In one specific, non-limiting example, from about 1 to about 50 nmol of a compound of the invention is administered, for example about 2 to about 20 nmol, for example about 10 nmol is administered as a subcutaneous injection. The exact dose is readily determined by one of skill in the art based on the potency of the specific compound utilized, the route of delivery of the compound and the age, weight, sex and physiological condition of the subject.

The doses discussed above may be given, for example, once, twice, three-times or four-times a day or once or twice a week. In some embodiments, a dose may be given no more frequently than once a week. Alternatively, they may be given once every 2, 3 or 4 days. According to certain embodiments they may be administered once shortly before each meal to be taken.

EXAMPLES

The invention is further described with reference to the following non-limiting examples.

Materials and Methods

Peptide Synthesis

Peptide synthesis was carried out on a tricyclic amide linker resin. Amino acids were attached using the Fmoc strategy. Each amino acid was added sequentially from the C- to the N-termini. Peptide couplings were mediated reagents such as TBTU. Peptide cleavage from the resin was achieved with trifluoracetic acid in the presence of scavengers.

Peptides were purified by reverse phase HPLC. Quality control was performed on all purified peptides and peptides were shown in most cases to be greater than 90% pure by HPLC in two buffer systems. MALDI-MS showed the expected molecular ion.

Receptor Potency of Peptides at the Human GLP-1 and Glucagon Receptors, Overexpressed in CHO Cells Biological activity was assessed by potency of peptides to stimulate cAMP production in Chinese Hamster Ovary (CHO) cell lines overexpressing the human GLP or the human glucagon receptor. Cells were plated at a density of $8\times10^{-5}$ cells/mL in serum free media, into 96 well half area plates, on the day of the assay. A commercial cAMP kit (Cisbio) was used to quantify cAMP in the cell via HTRF (Homogeneous Time-Resolved Fluorescence) technology after 30 mins of peptide stimulation and a further 1 h lysis. Plates were read on a SpectraMax i3x Multi-Mode Detection Platform plate reader and concentration response curves drawn with Graph Pad Prism 7.0. $EC_{50}$ values were generated for each peptide and compared to the controls for the day.

In Vitro Assessment of Peptide Stimulated Insulin Secretion

The amount of insulin secreted (released into the supernatant) by INS1 832/13 cells (rat pancreatic beta cells), following stimulation for 24 hours with a compound of the invention or a comparator compound or compounds (GLP-1, exendin-4, or liraglutide), was determined. INS1 832/13 cells were exposed to test compound at the indicated concentration in complete RPMI+11 mM glucose, following a prior 24 hour period in low glucose (3 mM) medium. The results were analysed by HTRF (Cisbio). The results were expressed as a fold insulin release relative to baseline insulin release on exposure to 11 mM glucose in the absence of test compound.

In Vivo Characterisation of Peptides

For repeat dosing studies, ab libitum fed male Wistar rats (Charles River) received a total of three subcutaneous injections of saline or example peptide of the invention (4 nmol/kg) over a 7 day period, a single injection on each of study days 1, 4 and 7. Total food intake from study day 1 to 11 and body weight change over the same period was calculated. For single dose studies, fasted (24 h) male Wistar rats (Charles River) received a single subcutaneous injections of saline or example peptide of the invention (either 5 or 10 nmol/kg). Total food intake from dosing to 48 or 72 h after dosing was measured, as was body weight change from pre-fasted to 48 or 72 h post dose.

Results

FIG. 1 shows a table providing amino acid sequences of example compounds of the invention. For example, the amino acid sequence of example compound no. 1 is as follows:

His-Aib-His-Gly-Thr-Phe-Thr-Ser-Asp-Tyr-Ser-Arg-
Tyr-Leu-Asp-Gln-Arg-Arg-Ala-Gln-Glu-Phe-Ile-Glu-
Trp-Leu-Leu-Ala-Thr-His-His-His-His-His-Pro-Ser-
NH2 i.e. the N-terminal residue of the amino acid sequence is a His residue, and the C-terminal residue is a Ser residue containing a —C(O)NH₂ group in place of the carboxylic acid group present in Ser.

FIG. 2 shows a table providing receptor potency data for example peptides at the human GLP-1 and glucagon receptors, overexpressed in Chinese hamster ovary (CHO) cells. Biological activity was assessed by the potency of peptides to stimulate cAMP production in the CHO cells. The values provided are the ratios of the example compound $EC_{50}$ to the native GLP-1 or glucagon $EC_{50}$. (e.g. for the "Average ratio to GLP-1±SEM" column, a value of 0.5 would indicate that the concentration of the example compound required to stimulate 50% maximum release of cAMP is half the concentration of native GLP-1 that is required, and a value of 2 would indicate that the concentration of the example compound required to stimulate 50% maximum release of cAMP is 2 times that of native GLP-1).

FIG. 3 provides exemplar graphs of peptide-stimulated cAMP production in cells over expressing the human GLP-1 receptor. $EC_{50}$ values were generated for each example peptide and compared to the controls for the day.

FIG. 4 provides exemplar graphs of peptide stimulated cAMP production in cells over expressing the human glucagon receptor. $EC_{50}$ values were generated for each peptide and compared to the controls for the day.

As can be seen from FIGS. 2, 3 and 4, the example compounds have greater activity at the glucagon receptor relative to native glucagon, than they have at the GLP-1 receptor relative to native GLP-1.

FIG. 5 shows a table summarising the results of an in vitro assessment of peptide-stimulated insulin secretion. Concentration of insulin in cell media following incubation of immortalised rat pancreatic beta cells, INS-1 832/13 cell line, stimulated for 24 h with test peptides. Values shown are $EC_{50}$ and $E_{max}$ relative to GLP-1 stimulated insulin release.

FIG. 6 provides exemplar graphs showing an In vitro assessment of peptide stimulated insulin secretion.

As can be seen from FIGS. 5 and 6, the example compounds demonstrate excellent insulin secretion effects: they have a higher $E_{max}$ and/or $EC_{50}$ than GLP-1 and than liraglutide. The compounds thus find use in the therapy of disorders such as diabetes.

Figure 7A:
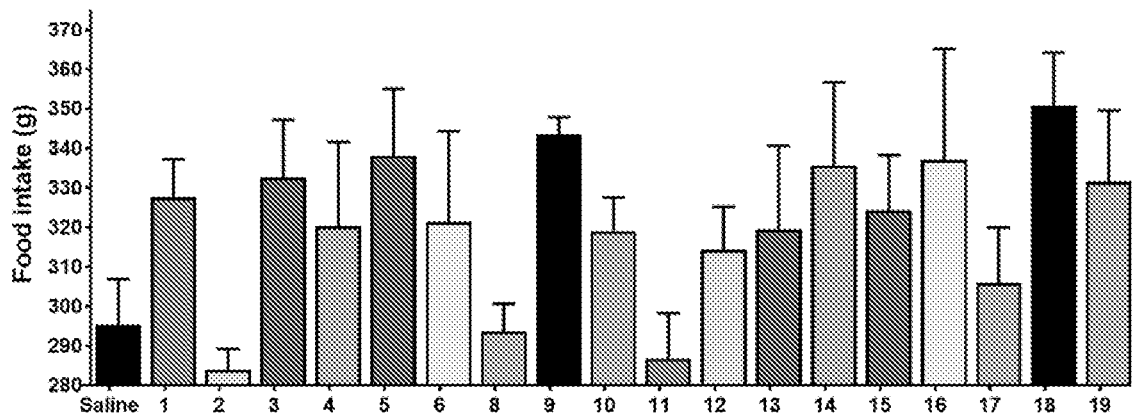
FIG. 7 shows results of in vivo feeding studies in Wistar rats allowed free access to food, and administered example compound of the invention, or administered saline.
Figure 7B:
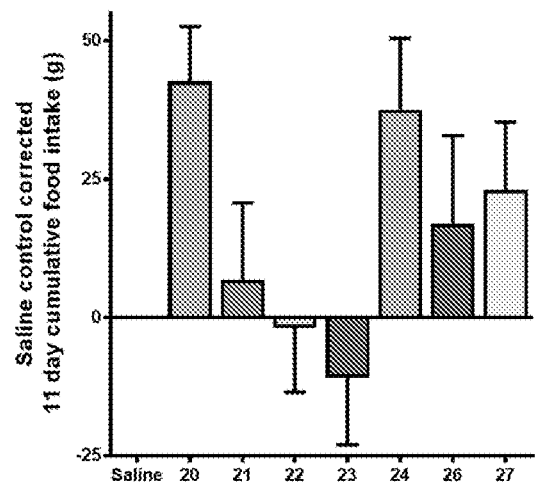

FIGS. 7 and 8 summarise the results of in vivo feeding studies in Wistar rats administered example peptides of the invention. FIG. 7 shows total food intake from study day 1 to 11 for each example peptide. The results for Example peptides 1 to 19 are shown in FIG. 7a; the results for Example peptides 20 to 24, 26 and 27 are shown in FIG. 7b. In FIG. 7a, the outcome for rats administered saline is also shown. In FIG. 7b, the food intake for the saline control animals has been subtracted from the intake in each experiment, such that the bar in the figure represents the difference from the control. The result shown by the bars is referred to as the "saline control corrected" intake value.

Figure 8A:
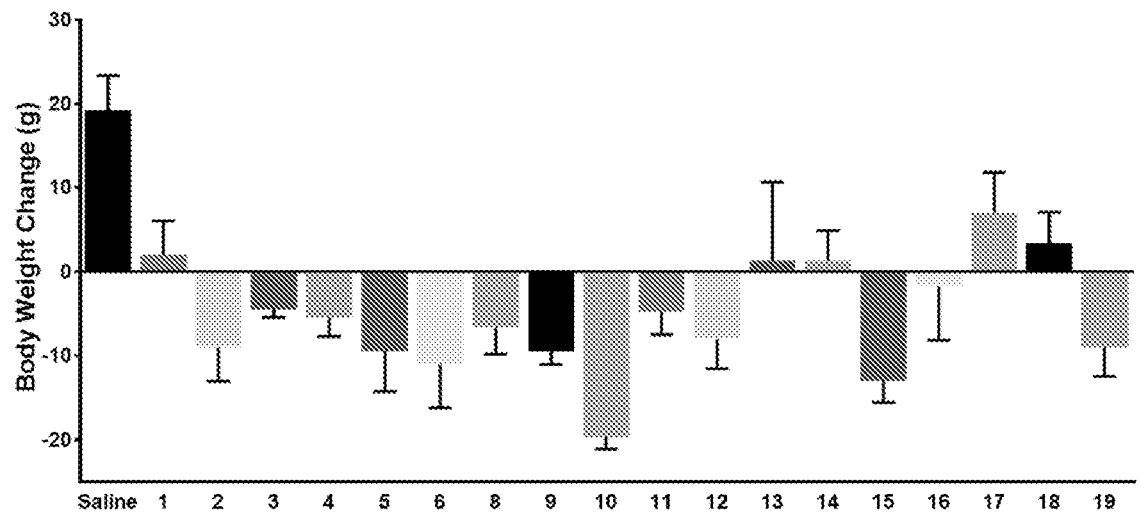
FIG. 8 shows results of in vivo feeding studies in Wistar rats allowed free access to food, and administered example compound of the invention, or administered saline.
Figure 8B:
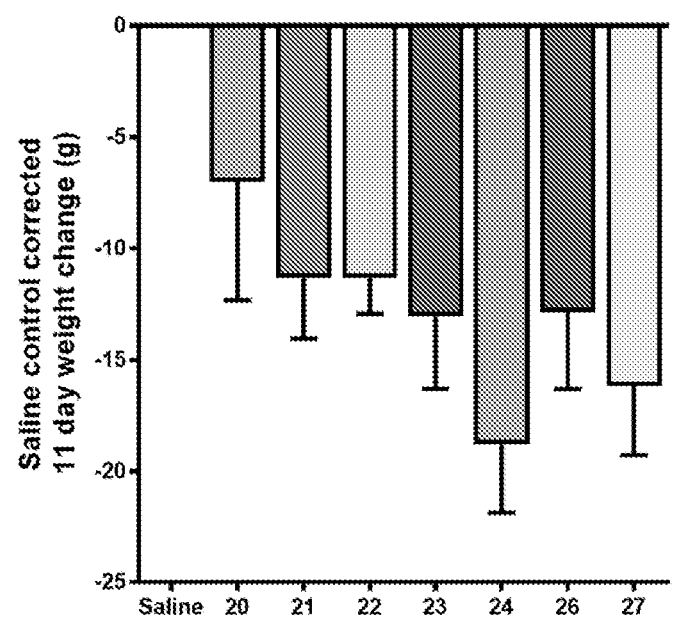

FIG. 8 shows body weight change from study day 1 to 11 for each example peptide, and for rats administered saline also. The results for Example peptides 1 to 19 are shown in FIG. 8a; the results for Example peptides 20 to 24, 26 and 27 are shown in FIG. 8b. In FIG. 8a, the outcome for rats administered saline is also shown. In FIG. 8b, the weight change for the saline control animals has been subtracted from the change of the treatment group in each experiment, such that the bar in the figure represents the difference from the saline control group. The result shown by the bars is referred to as the "saline control corrected" change value.

As can be seen from FIGS. 7 and 8, rats which were given free access to food and which were administered example peptides of the invention, achieved reduced weight gain or achieved weight loss compared with rats which were administered saline. This supports that the compounds of the invention are particularly effective at improving metabolism, and that they find use in the therapy of disorders such as obesity. However, the amount of food consumed by rats which were administered zo the example peptides was similar to or greater than the amount of food consumed by rats which were administered saline. The absence of, or only minimal, effect on amount of food ingested supports that the compounds have reduced side effects relating to nausea. As discussed above, rodents are not able to vomit, but those experiencing nausea are likely to be put off from consuming food. With the peptides of the invention, there was no observed evidence of the animals being put off consuming food.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A compound having an amino acid sequence of formula (I):

His-Aib-His-Gly-Thr-Phe-Thr-Ser-Asp-Tyr-Ser-Xaa12- (SEQ ID NO: 28)
Tyr-Leu-Asp-Xaa16-Xaa17-Arg-Ala-Xaa20-Xaa21-Phe-
Ile-Glu-Trp-Leu-Leu-Xaa28-Xaa29-V (I)

wherein
Xaa12 is Lys or Arg;
Xaa16 is Ala, Gln, Glu, His or Thr;
Xaa17 is Lys or Arg;
Xaa20 is Gln or His;
Xaa21 is Glu or Asp;
Xaa28 is Gln, Asn, His, Ala, Thr, Leu, Ser or Ile;
Xaa29 is Ser, Thr or Gly;
and
V is a sequence consisting of from 5 to 12 amino acid residues, wherein at least 4 of said amino acid residues are His residues, and wherein the carboxylic acid group of the amino acid residue at the C-terminus may optionally be replaced by a —C(O)NH$_2$ group;
or a derivative of the compound;
or a salt of the compound or the derivative.

2. The compound as claimed in claim 1, wherein Xaa12 is Arg.

3. The compound as claimed in claim 1, wherein Xaa12 is Lys.

4. The compound claimed in claim 1, wherein Xaa16 is Gln, Glu or Ala.

5. The compound as claimed in claim 1, wherein Xaa17 is Arg.

6. The compound as claimed in claim 1, wherein Xaa17 is Lys.

7. The compound as claimed in claim 1, wherein Xaa20 is Gln.

8. The compound as claimed in claim 1, wherein Xaa21 is Glu.

9. The compound as claimed in claim 1, wherein Xaa29 is Thr or Gly.

10. The compound as claimed in claim 1, wherein Xaa29 is Ser.

11. The compound as claimed in claim 1, wherein V is a C-terminal sequence of formula (II):

His-His-His-His-His (SEQ ID NO: 35)-Z        (II)

wherein Z is a sequence of from 1 to 6 amino acid residues, and wherein a carboxylic acid group of the amino acid residue at the C-terminus may optionally be replaced by a —C(O)NH$_2$ group.

12. The compound as claimed in claim 1, wherein
Xaa12 is Arg or Lys;
Xaa16 is Gln, Glu, His or Ala;
Xaa17 is Arg or Lys;
Xaa20 is Gln or His;
Xaa21 is Glu;
Xaa28 is Asn, His, Ala, Thr, Leu or Gln;
Xaa29 is Thr, Gly or Ser;
V is a C-terminal sequence of formula (II):

His-His-His-His-His (SEQ ID NO: 35)-Z        (II)

wherein Z is a sequence of from 1 to 6 amino acid residues, and
wherein a carboxylic acid group of the amino acid residue at the C-terminus may optionally be replaced by a —C(O)NH$_2$ group.

13. The compound as claimed in claim 1, wherein V is selected from the group consisting of:

His-His-His-His-His-Pro-Ser-Trp;    (SEQ ID NO: 36)

His-His-His-His-His-Ser;    (SEQ ID NO: 37)

His-His-His-His-His-Val;    (SEQ ID NO: 38)

His-His-His-His-His-Ser-Val;    (SEQ ID NO: 39)

His-His-His-His-His-Ser-Trp;    (SEQ ID NO: 40)

His-His-His-His-His-Pro-Ser;    (SEQ ID NO: 41)

His-His-His-His-His-Pro-Thr;    (SEQ ID NO: 42)

-continued

His-His-His-His-His-Leu-Ser; (SEQ ID NO: 43)

His-His-His-His-His-Thr-Thr; (SEQ ID NO: 44)

His-His-His-His-His-Gln-Trp; (SEQ ID NO: 45)

His-His-His-His-His-Pro-Ser-C(O)NH$_2$; (SEQ ID NO: 46)

His-His-His-His-His-Gln-Gly-Trp; (SEQ ID NO: 47)

His-His-His-His-His-Gly-Gln-Trp; (SEQ ID NO: 48)

His-His-His-His-His-Gly-Leu-Ser; (SEQ ID NO: 49)

His-His-His-His-His-Gly-Pro-Thr; (SEQ ID NO: 50)

His-His-His-His-His-Pro-Ser-Gly-Trp; (SEQ ID NO: 51)

His-His-His-His-His-Ser-Val-Pro-Pro-Pro-C(O)NH$_2$; (SEQ ID NO: 52)

His-His-His-His-His-Val-Ser-Pro-Pro-Pro-Trp; and (SEQ ID NO: 53)

His-His-His-His-His-Ser-Val-Pro-Pro-Pro-Trp. (SEQ ID NO: 54)

14. The compound as claimed in claim 1, wherein the compound comprises an amino acid sequence corresponding to any one of the amino acid sequences of SEQ ID Nos: 1-27.

15. A method, comprising administering a compound, a derivative or a salt thereof as claimed in claim 1 or claim 14 to a subject in need of weight reduction.

16. The compound as claimed in claim 14, wherein the compound comprises an amino acid sequence corresponding to the amino acid of SEQ ID NO. 24.

17. The compound as claimed in claim 1, wherein the derivative, or a salt of such a derivative comprises one or more derivatizations selected from amidation, glycosylation, carbamylation, acylation, sulfation, phosphorylation, cyclization, lipidization, PEGylation and fusion to another peptide or protein to form a fusion protein.

18. A composition comprising a compound, a derivative or a salt thereof as claimed in claim 1 together with a pharmaceutically acceptable carrier and optionally a further therapeutic agent.

19. The composition as claimed in claim 18, wherein the composition is present in a syringe or other administration device for subcutaneous administration to humans.

20. A method of treating or preventing a disease or disorder or other non-desired physiological state selected from (i) treating diabetes, obesity or non-alcoholic fatty liver disease in a subject, (ii) increasing energy expenditure in a subject, improving insulin release in a subject, improving carbohydrate metabolism in a subject, reducing appetite, reducing food intake, reducing calorie intake, or (iii) combinations thereof in a subject;

comprising administering a therapeutically effective amount of a compound, a derivative or a salt thereof as claimed in claim 1 to a subject in need thereof.

\* \* \* \* \*

UNITED STATES PATENT AND TRADEMARK OFFICE
CERTIFICATE OF CORRECTION

| | | |
|---|---|---|
| PATENT NO. | : 11,591,380 B2 | Page 1 of 1 |
| APPLICATION NO. | : 16/769774 | |
| DATED | : February 28, 2023 | |
| INVENTOR(S) | : Bloom | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 16 days.

Signed and Sealed this
Seventh Day of January, 2025

Derrick Brent
*Acting Director of the United States Patent and Trademark Office*